US009303044B2

(12) United States Patent
Coller et al.

(10) Patent No.: US 9,303,044 B2
(45) Date of Patent: Apr. 5, 2016

(54) 7-(PIPERAZIN-1-YL)-5H-[1,3,4]THIADIAZOLO[3,2-A]PYRIMIDIN-5-ONES FOR THE TREATMENT OF THROMBOTIC DISORDERS

(71) Applicants: The Rockefeller University, New York, NY (US); The United States of America, as Represented by the Secretary, Department of Health and Human Services, Washington, DC (US); Mount Sinai School of Medicine, Office of Technology and Business Development, New York, NY (US)

(72) Inventors: Barry S. Coller, New York, NY (US); Craig Thomas, Rockville, MD (US); Marta Filizola, New York, NY (US); Joshua McCoy, Portland, ME (US); Wenwei Huang, Rockville, MD (US); Min Shen, Boyds, MD (US); Jian-Kang Jiang, Columbia, MD (US)

(73) Assignees: THE UNITED STATES OF AMERICA AS REPRESENTED BY THE SECRETARY, DEPARTMENT OF HEALTH AND HUMAN SERVICES, Washington, DC (US); THE ROCKEFELLER UNIVERSITY, New York, NY (US); ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 14/372,488

(22) PCT Filed: Jan. 16, 2013

(86) PCT No.: PCT/US2013/021749
§ 371 (c)(1),
(2) Date: Jul. 16, 2014

(87) PCT Pub. No.: WO2013/109632
PCT Pub. Date: Jul. 25, 2013

(65) Prior Publication Data
US 2015/0050325 A1 Feb. 19, 2015

Related U.S. Application Data

(60) Provisional application No. 61/587,030, filed on Jan. 16, 2012.

(51) Int. Cl.
| | | |
|---|---|---|
| *A01N 43/90* | (2006.01) | |
| *A61K 31/519* | (2006.01) | |
| *C07D 471/00* | (2006.01) | |
| *C07D 487/00* | (2006.01) | |
| *C07D 491/00* | (2006.01) | |
| *C07D 513/04* | (2006.01) | |
| *A61K 45/06* | (2006.01) | |
| *A61K 31/436* | (2006.01) | |

(Continued)

(52) U.S. Cl.
CPC ............ *C07D 513/04* (2013.01); *A61K 31/337* (2013.01); *A61K 31/436* (2013.01); *A61K 31/4353* (2013.01); *A61K 31/519* (2013.01); *A61K 31/727* (2013.01); *A61K 45/06* (2013.01); *A61L 31/022* (2013.01); *A61L 31/10* (2013.01); *A61L 31/16* (2013.01); *A61L 2300/416* (2013.01); *A61L 2300/42* (2013.01); *A61L 2300/45* (2013.01)

(58) Field of Classification Search
None
See application file for complete search history.

(56) References Cited

U.S. PATENT DOCUMENTS

| 4,265,898 A | 5/1981 | Horstmann et al. |
| 4,548,938 A | 10/1985 | Kennis et al. |

(Continued)

FOREIGN PATENT DOCUMENTS

| WO | 2008057601 A2 | 5/2008 |
| WO | 2009024615 A1 | 2/2009 |

(Continued)

OTHER PUBLICATIONS

International Preliminary Report on Patentability for International Patent Application No. PCT/US2013/021749; International Filing Date: Jan. 16, 2013; Date of Mailing: May 14, 2015; 2 Pages.
Written Opinion of the International Searching Authority; International Application No. PCT/US2013/021749; International Filing Date: Jan. 16, 2013; Date of Mailing: Apr. 26, 2013; 5 pages.
Basani et al. "Species differences in small molecule binding to allbβ3 are the result of sequence differences in 2 loops of the allb β propeller" Blood, vol. 113, (2009), pp. 902-910.
Blue et al., "Application of high-Throughput Screening to Identify a Novel a IIb-Specific Small-Molecule Inhibitor of allbβ3-Mediated Platelet Interaction with Fibrinogen" Blood, vol. 111, No. 3, Feb. 1, 2008, pp. 1248-1256.
Blue et al., "Structural and Thereapeutic Insights From the Species Specifically and in Vivo Antithrombotic Activity of a Novel a IIb-specific allbβ3 Antagonist", Blood, vol. 114, No. 1, Jul. 2, 2009, pp. 195-201.
Chemical Abstract RN 946692-19-9. Retrieved from STN Mar. 25, 2014.

(Continued)

*Primary Examiner* — Jeffrey H Murray
(74) *Attorney, Agent, or Firm* — Cantor Colburn LLP

(57) ABSTRACT

The present invention relates to compounds and compositions of Formula P useful for inhibiting and/or reducing platelet deposition, adhesion and/or aggregation. The definitions of variables A, B, $R_2$, $R_3$, $R_4$, $R_a$, $R_a'$, $R_b$, $R_b'$, $R_c$, $R_d$, $R_d'$, $R_e$, and $R_e'$ are provided in the disclosure. The present invention further relates to methods for the treatment or prophylaxis of thrombotic disorders, including stroke, myocardial infarction, unstable angina, peripheral vascular disease, abrupt closure following angioplasty or stent placement and thrombosis as a result of vascular surgery.

20 Claims, No Drawings

(51) Int. Cl.
A61K 31/337 (2006.01)
A61K 31/4353 (2006.01)
A61K 31/727 (2006.01)
A61L 31/02 (2006.01)
A61L 31/10 (2006.01)
A61L 31/16 (2006.01)

(56) References Cited

U.S. PATENT DOCUMENTS

| | | | |
|---|---|---|---|
| 8,173,661 | B2 | 5/2012 | Blue et al. |
| 9,066,948 | B2 * | 6/2015 | Cotler et al. |
| 2010/0150913 | A1 | 6/2010 | Blue et al. |

FOREIGN PATENT DOCUMENTS

| | | | | |
|---|---|---|---|---|
| WO | 2012009688 A1 | 1/2012 | | |
| WO | WO2012009688 A1 * | 1/2012 | ........... | A61K 31/497 |

OTHER PUBLICATIONS

Eslin et al., "Transgenic mice studies demonstrate a role for platelet factor 4 in thrombosis: dissociation between anticoagulant and antithrombotic effect of heparin" Blood, vol. 104 (2004), pp. 3173-3180.

European Search Report and Supplemental Search Report for European Patent Application No. 11807604.1, Date of Mailing: Nov. 28, 2013, 11 Pages.

International Search Report of the International Searching Authority for International Patent Application No. PCT/US2011/44267, International Filing Date: Jul. 15, 2011, Date of Mailing: Dec. 6, 2011, 3 Pages.

Jiang et al., "A Novel Class of Ion Displacement Ligands as Antagonista of the allbβ3 Receptor That Limit Conformational Reorganization of the Receptor", Bioorganic & Medicinal Chemistry Letters; 24, (2014); pp. 1148-1153.

Law et al., "Genetic and Pharmacological Analyses of Syk Function in allbβ3 Singnaling in Platelets" Blood, vol. 93, (1999), pp. 2645-2652.

McCoy et al., "Inhibitors of Platelet Integrin allbβ3" Probe Reports from the NIH Molecular Libraries Program—NCBI Bookshelf; Mar. 27, 2010, http://www.ncbi.nlm.nih.gov/books/NBK56230/#ml165.s1; 17 Pages.

Negri et al., "Structure-Based Virtual Screening of Small-Molecule Antagonists of Platelet Integrin allbβ3 that do not Prime the Receptor to Bind Ligand" Journal of Computer-Aided Molecular Design; vol. 26, Issue 9, Sep. 2012, Abstract Only.

Neyman et al. "Analysis of the spatial and temporal characteristics of platelet-delivered factor VIII-based clots" Blood, vol. 112, (2008), pp. 1101-1108.

Thornton et al., "Identification of distal regulator regions in the human allb gene locus necessary for consistent, high-level megakaryocyte expression" Blood, vol. 100, (2002), pp. 3588-3596.

Written Opinion of the International Searching Authority for International Patent Application No. PCT/US2011/44267, Issued Dec. 6, 2011.

Yarovoi et al. "Factor VIII ectopically expressed in platelets: eficacy in hemophilia A treatment" Blood, vol. 102, (2003), pp. 4006-4013.

Zhu et al., "Structure-Guided Design of a High-Affinity Platelet Intergin allbβ3 Receptor Antagonist That Disrupts MG2 + Binding to the MIDAS" Science Translational Medicine, vol. 4, Issue 125, Mar. 14, 2012, age 125ra32, Abstract Only.

International Search Report of the International Searching Authority for International Patent Application No. PCT US2013/21749; International Filing Date: Jan. 16, 2013; Date of mailing: Apr. 26, 2013; 4 Pages.

* cited by examiner

7-(PIPERAZIN-1-YL)-5H-[1,3,4]THIADIAZOLO[3,2-A]PYRIMIDIN-5-ONES FOR THE TREATMENT OF THROMBOTIC DISORDERS

CROSS REFERENCE TO RELATED APPLICATIONS

This application is a U.S. National Stage application filed under §371(e) of PCT/US2013/021749, filed Jan. 16, 2013, which claims priority from U.S. Provisional Application No. 61/587,030, filed on Jan. 16, 2012, the contents of which are incorporated by reference in their entirety.

The present invention was made with funding from National Institute of Health of Grant Nos. HL19278, U54CA143930 and MH083257. The United States Government has certain rights in this invention.

FIELD OF THE INVENTION

The present invention relates to compounds and compositions useful for inhibiting or reducing platelet deposition, adhesion and/or aggregation. The present invention further relates to drug-eluting stent and methods of treatment or prophylaxis of thrombotic disorders, including stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

BACKGROUND

Platelet accumulation at sites of vascular injury is a dynamic process that mediates formation of both the primary hemostatic plug and pathologic thrombus formation. The mechanisms by which platelet surface proteins direct platelet recruitment to thrombi under flow conditions have been studied in detail. In addition to directing initial platelet adhesion, cell-surface receptor interactions activate intracellular signaling. Intracellular signaling stimulates the release of thrombogenic substances from platelet granules. Signaling also mediates activation of the platelet integrin $\alpha IIb\beta 3$ that facilitates firm adhesion of the platelets at the sites of injury.

Arterial thrombosis mediates tissue infarction in coronary artery disease, cerebrovascular disease, and peripheral vascular disease, and, thus, is the single most common cause of morbidity and mortality in the United States. Platelets are key mediators of arterial thrombosis. Thus, the identification of compounds that inhibit platelet function is of great importance to medicine.

Platelets form the body's primary means of hemostasis and, as such, have developed an elaborate mechanism of surveying the vasculature for defects in endothelial integrity. This mechanism involves the ability to respond to subendothelial matrices, shear forces, neighboring platelets, the adrenal axis, as well as soluble proteinacious, nucleotide, and lipid signals. Despite this plethora of physiologic activators, the platelet has only a small repertoire of major functional outputs. Upon activation, platelets change shape, aggregate, and secrete their granular contents. The process of platelet activation involves the expression of activities not shared by functionally intact resting platelets, including, for example, ATP release, serotonin release, lysosomal release, alpha granule release, dense granule release, and cell surface expression of markers of activated platelets [including, but not limited to P-selectin and activated $\alpha IIb\beta 3$ (GPIIb/IIIa) receptor]. In addition, platelet activation results in the aggregation of platelets with each other and attachment to non-platelet surrounding cells. The granular contents of platelets supply additional adhesion molecules, growth factors, coagulation enzymes and other specialized molecules instrumental in the process of thrombus formation and the initiation of the healing process.

In addition to coronary artery disease/myocardial infarction, cerebrovascular disease and peripheral vascular disease, diseases and disorders associated with inappropriate platelet activity and arterial thrombosis also include, for example, stable and unstable angina, transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation. Inhibitors of platelet activity can provide therapeutic and preventive benefits for each of these diseases or disorders. It is also possible that inappropriate platelet activation plays a role in venous thrombosis, such that platelet inhibitors can be useful for the treatment or prophylaxis of disorders associated with such thromboses.

A connection is emerging between platelet activation and inflammation, particularly allergic inflammation (e.g., in asthma) and inflammation at the sites of atherosclerotic damage. Therefore, compounds that inhibit platelet activation can also be useful in the treatment or prophylaxis of disorders involving inflammation.

There are a number of agents presently available that target platelet function. For example, aspirin is a relatively weak platelet inhibitor. However, aspirin can cause life-threatening allergic reactions in sensitive individuals.

Another platelet inhibiting agent is ticlopidine (Ticlid™, Roche Pharmaceuticals). Because it requires the production of active metabolites to be effective, the effect of ticlopidine is delayed 24-48 hours. The drug can also cause thrombotic thrombocytopenic purpura as well as life threatening leukopenia, nausea, abdominal pain, dyspepsia, diarrhea and skin rash.

Clopidogrel (Plavix™, Bristol-Meyers Squibb/Sanofi Pharmaceuticals) is another platelet inhibitor that requires the generation of active metabolites for its therapeutic efficacy. Therefore, clopidogrel also has a delay of at least several hours for its effect. Clopidogrel can also cause thrombotic thrombocytopenia purpura. The drug has also been associated with a number of side effects, including rash, edema, hypertension, hypercholesterolemia, nausea, abdominal pain, dyspepsia, diarrhea, urinary tract infections, liver enzyme elevations and arthralgia.

Prasugrel and ticagrelor have been approved as $P2Y_{12}$ inhibitors for use as a platelet inhibitor, but similar to clopidogrel, major bleeding, including non-fatal as well as fatal bleeding was observed.

The platelet inhibitory agent abciximab (c7E3 Fab, Reopro®, manufacturer-Centocor B. V., distributor-Eli Lilly and Co.) is only available in a parenteral form. The drug can cause severe thrombocytopenia. Its antiplatelet effects last for several days unless platelet transfusions are given and, therefore, may complicate surgery that is sometimes required in the setting of life-threatening arterial occlusion (e.g., emergent cardiac surgery in the setting of a myocardial infarction).

There is only limited clinical experience with the oral anti-$\alpha IIb\beta 3$ agents lamifiban, sibrafiban, orbofiban and xemilofiban, none of which are approved for human use. Similarly, clinical experience is limited with the phosphodiesterase inhibitors cilostazol, trapidil and trifusal. There is more clinical experience with the phosphodiesterase inhibitor dipyridamole, but its activity is relatively weak and so it is not frequently used unless combined with aspirin.

There is a need in the art for additional platelet adhesion and aggregation inhibitory agents for the treatment and prophylaxis of diseases or disorders associated with abnormalities in platelet adhesion and aggregation.

It is known that integrin αIIbβ3 is a receptor on the surface of human platelets. As a heterodimeric complex composed of both αIIb and β3 subunits, the dimer is responsible for binding adhesive plasma proteins, most notably fibrinogen and von Willebrand factor (vWF). The binding of fibrinogen, vWF and other ligands by αIIbβ3 is mediated principally though the peptide recognition sequence Arg-Gly-Asp (RGD) or the fibrinogen η chain dodecapeptide HHLG-GAKQAGDV. Conformational changes in αIIbβ3 are thought to occur upon the binding of ligand to the receptor, leading to the exposure of ligand-induced binding sites (LIBS) as detected by LIBS-specific monoclonal antibodies (mAbs). Electron microscopy and crystal structures of the integrin in complex with various R(K)GD-like ligands support the theory that the integrin undergoes a major conformational change after or during ligand binding.

Currently two small molecule inhibitors of the αIIbβ3 exist: a cyclic homoarginine-glycine-aspartic acid peptide (eptifibatide) and an RGD peptidomimetic (tirofiban). Both inhibitors act by competitively blocking the binding site for fibrinogen. Although both compounds have demonstrated significant clinical benefit, tirofiban (Aggrastat™, Merck and Co., Inc.) is only available in a parenteral form and can cause thrombocytopenia, dizziness and vasovagal reactions. Eptifibatide (Integrilin™, COR Therapeutics, Inc., Key Pharmaceuticals Inc.) is also only available for parenteral administration and it too can cause thrombocytopenia and hypotension. Crystal structure studies of the αIIbβ3 headpiece demonstrates that these inhibitors bind to both αIIb and to the divalent cation in the β3 subunit's metal ion dependant adhesion site (MIDAS). It is believed that the interaction with the MIDAS metal ion induces conformational changes in the β3 which leads to the increased the risk for thrombotic complications following αIIbβ3 inhibitor therapy.

SUMMARY OF THE INVENTION

Previously, our scientists have identified inhibitors of αIIbβ3 that are capable of inhibiting fibrinogen binding and platelet aggregation without inducing the binding of one or more integrin β3 LIBS-specific monoclonal antibodies (mAbs). These inhibitors are disclosed in U.S. patent application Ser. No. 12/514,286 (U.S. Pub. No. 2010/0150913, now U.S. Pat. No. 8,173,661) and PCT/US11/44267, the contents of each of which are hereby incorporated by reference in their entirety. Our scientists have now identified further inhibitors of αIIbβ3 that are capable of inhibiting fibrinogen binding and platelet aggregation without inducing the binding of integrin β3 LIBS. The present invention thus provides αIIbβ3 antagonists, pharmaceutical compositions, drug-eluting stent comprising αIIbβ3 antagonists and new methods of treatment and prophylaxis using αIIbβ3 antagonists.

In the first aspect, the invention provides a compound of Formula P:

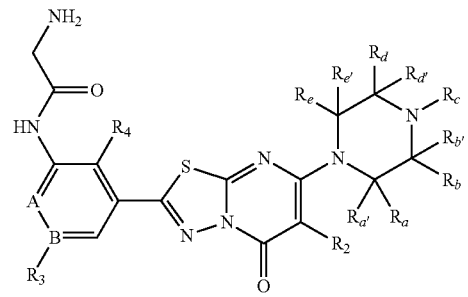

Formula P wherein:
i) A is carbon or nitrogen;
ii) B is carbon or nitrogen, provided that when B is nitrogen, $R_3$ does not exist;
iii) $R_2$ is H or halo (e.g., fluoro);
iv) $R_a$, $R_a'$, $R_b$, $R_b'$, $R_c$, $R_d$, $R_d'$, $R_e$, and $R_e'$ are H;
v) $R_3$ and $R_4$ are independently hydrogen, halo (e.g., bromo), $C_{1-4}$alkyl (e.g., methyl, ethyl, ethenyl (—CH═CH$_2$), propenyl (—C(CH)═CH$_2$) or isopropyl), halo$C_{1-4}$alkyl (e.g., CF$_3$), hydroxy-$C_{1-4}$alkyl (—C(H)(OH)CH$_3$ or —CH$_2$(OH)) or acetyl, provided $R_3$ and $R_4$ are not both hydrogen when A and B are both carbon;
in free or salt form.

In a further embodiment, the compound of Formula P is a compound of Formula I:

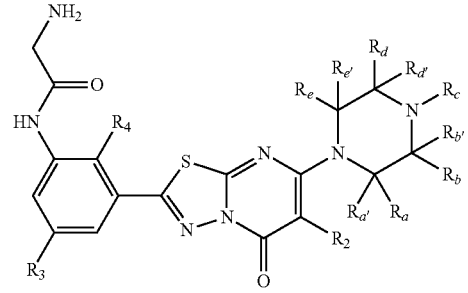

Formula I wherein:
vi) $R_2$ is H;
vii) $R_a$, $R_a'$, $R_b$, $R_b'$, $R_c$, $R_d$, $R_d'$, $R_e$, and $R_e'$ are H;
viii) $R_3$ and $R_4$ are independently hydrogen, halo (e.g., bromo), $C_{1-4}$alkyl (e.g., methyl, ethyl, ethenyl (—CH═CH$_2$), propenyl (—C(CH)═CH$_2$) or isopropyl), halo$C_{1-4}$alkyl (e.g., CF$_3$), hydroxy-$C_{1-4}$alkyl (—C(H)(OH)CH$_3$) or acetyl, provided $R_3$ and $R_{49}$ are not both hydrogen;
in free or salt form.

In another further embodiment of the first aspect, the invention provides the compound of Formula P and Formula I as follows:
1.1. the compound of Formula P or Formula I, wherein $R_3$ and $R_4$ are independently halo (e.g., bromo);
1.2. the compound of Formula P or Formula I, or 1.1, wherein $R_3$ and $R_4$ are independently bromo;
1.3. the compound of Formula P or Formula I, wherein $R_3$ and $R_4$ are independently $C_{1-4}$alkyl (e.g., methyl, ethyl, ethenyl (—CH═CH$_2$), propenyl (—C(CH)═CH$_2$) or isopropyl);

1.4. the compound of Formula P or Formula I, or 1.3, wherein $R_3$ and $R_4$ are independently is methyl;
1.5. the compound of Formula P or Formula I, or 1.3, wherein $R_3$ and $R_4$ are independently ethyl;
1.6. the compound of Formula P or Formula I, or 1.3, wherein $R_3$ and $R_4$ are independently ethenyl (—CH=CH$_2$);
1.7. the compound of Formula P or Formula I, or 1.3, wherein $R_3$ and $R_4$ are independently propenyl (—C(CH)=CH$_2$);
1.8. the compound of Formula P or Formula I, or 1.3, wherein $R_3$ and $R_4$ are independently isopropyl;
1.9. the compound of Formula P or Formula I, or 1.3, wherein $R_3$ and $R_4$ are independently haloC$_{1-4}$alkyl (e.g., CF$_3$);
1.10. the compound of Formula P or Formula I, or 1.3, wherein $R_3$ and $R_4$ are independently hydroxy-C$_{1-4}$alkyl (2-hydroxyethyl) or acetyl;
1.11. the compound of Formula P or Formula I, or 1.3, wherein $R_3$ and $R_4$ are independently 2-hydroxyethyl;
1.12. the compound of Formula P or Formula I, or 1.3, wherein $R_3$ and $R_4$ are independently acetyl;
1.13. the compound of Formula P or Formula I, wherein either $R_3$ or $R_4$ is hydrogen and the other R substitutent is halo (e.g., bromo), C$_{1-4}$alkyl (e.g., methyl, ethyl, ethenyl (—CH=CH$_2$), propenyl (—C(CH)=CH$_2$) or isopropyl), haloC$_{1-4}$alkyl (e.g., CF$_3$), hydroxy-C$_{1-4}$alkyl (—C(H)(OH)CH$_3$) or acetyl;
1.14. the compound of Formula P or Formula I or 1.13, wherein either $R_3$ or $R_4$ is hydrogen and the other R substitutent is as described in any of formulae 1.1-1.13;
1.15. the compound of Formula P or Formula 1.13 or 1.14, wherein $R_3$ is hydrogen;
1.16. the compound of Formula P or Formula I or any of formulae 1.13, 1.14 or 1.15, wherein $R_3$ is hydrogen and $R_4$ is C$_{1-4}$alkyl;
1.17. the compound of Formula P or Formula I or any of formulae 1.13-1.16, wherein $R_3$ is hydrogen and $R_4$ is methyl;
1.18. the compound of Formula P or Formula I or any of formulae 1.13-1.16, wherein $R_3$ is hydrogen and $R_4$ is ethyl;
1.19. the compound of Formula P or Formula I or any of formulae 1.13 or 1.14, wherein $R_4$ is hydrogen and $R_3$ is halo (e.g., bromo), C$_{1-4}$alkyl (e.g., methyl, ethyl, ethenyl (—CH=CH$_2$), propenyl (—C(CH)=CH$_2$) or isopropyl), haloC$_{1-4}$alkyl (e.g., CF$_3$), hydroxy-C$_{1-4}$alkyl (—C(H)(OH)CH$_3$) or acetyl;
1.20. the compound of Formula P or Formula I or any of formuale 1.13, 1.14 or 1.19, wherein $R_4$ is hydrogen and $R_3$ is as described in any of formulae 1.1-1.12;
1.21. the compound of Formula P or Formula I or any of formulae 1.13, 1.14 or 1.19, wherein $R_4$ is hydrogen and $R_3$ is C$_{1-4}$alkyl;
1.22. the compound of Formula P or Formula I or any of formulae 1.13, 1.14, 1.19 or 1.20, wherein $R_4$ is hydrogen and $R_3$ is methyl;
1.23. the compound of Formula P or Formula I or any of formulae 1.13, 1.14, 1.19 or 1.20, wherein $R_4$ is hydrogen and $R_3$ is ethyl;
1.24. the compound of Formula P or Formula I or formula 1.3, wherein $R_3$ and $R_4$ are C$_{1-4}$alkyl;
1.25. the compound of Formula P or Formula 1.24, wherein $R_4$ is methyl;
1.26. the compound of Formula P or Formula 1.24, wherein $R_4$ is ethyl;
1.27. the compound of Formula P or Formula 1.24, 1.25 or 1.26, wherein $R_3$ is methyl;
1.28. the compound of Formula P or any of formulae 1.1-1.27, wherein A is carbon or nitrogen;
1.29. the compound of Formula P or any of formulae 1.1-1.28, wherein A is carbon;
1.30. the compound of Formula P or any of formulae 1.1-1.28, wherein A is nitrogen;
1.31. the compound of Formula P or any of formulae 1.1-1.29, wherein B is carbon or nitrogen, provided that when B is nitrogen, $R_3$ does not exist;
1.32. the compound of Formula P or any of formulae 1.1-1.29, wherein B is carbon;
1.33. the compound of Formula P or any of formulae 1.1-1.29, wherein B is nitrogen and $R_3$ does not exist;
1.34. the compound of Formula P or any of formulae 1.1-1.14, 1.19, 1.25-1.33, wherein $R_3$ is —CH$_2$(OH);
1.35. the compound of Formula P, or any of formulae 1.1-1.34, wherein $R_2$ is H;
1.36. the compound of Formula P, or any of formulae 1.1-1.34, wherein $R_2$ is halo (e.g., fluoro);
1.37. the compound of Formula P wherein:
  i) A is nitrogen;
  ii) B is carbon;
  iii) $R_2$ is H or halo (e.g., fluoro);
  iv) $R_a$, $R_a'$, $R_b$, $R_b'$, $R_c$, $R_d$, $R_d'$, $R_e$, and $R_e'$ are H;
  v) $R_3$ and $R_4$ are independently hydrogen, halo (e.g., bromo), C$_{1-4}$alkyl (e.g., methyl, ethyl, ethenyl (—CH=CH$_2$), propenyl (—C(CH)=CH$_2$) or isopropyl), haloC$_{1-4}$alkyl (e.g., CF$_3$), hydroxy-C$_{1-4}$alkyl (—C(H)(OH)CH$_3$ or —CH$_2$(OH)) or acetyl;
1.38. The compound of Formula P wherein:
  i) A is carbon;
  ii) B is nitrogen and $R_3$ does not exist;
  iii) $R_2$ is H or halo (e.g., fluoro);
  iv) $R_a$, $R_a'$, $R_b$, $R_b'$, $R_c$, $R_d$, $R_d'$, $R_e$, and $R_e'$ are H;
  v) $R_4$ is hydrogen, halo (e.g., bromo), C$_{1-4}$alkyl (e.g., methyl, ethyl, ethenyl (—CH=CH$_2$), propenyl (—C(CH)=CH$_2$) or isopropyl), haloC$_{1-4}$alkyl (e.g., CF$_3$), hydroxy-C$_{1-4}$alkyl (—C(H)(OH)CH$_3$ or —CH$_2$(OH)) or acetyl;
1.39. the compound of Formula P, wherein said compound is selected from:

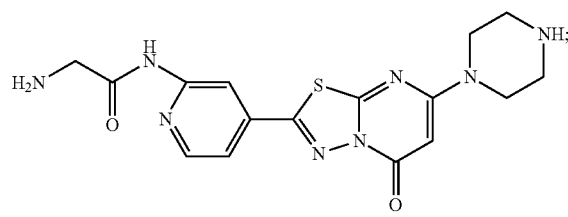

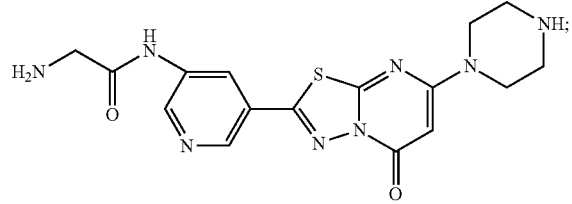

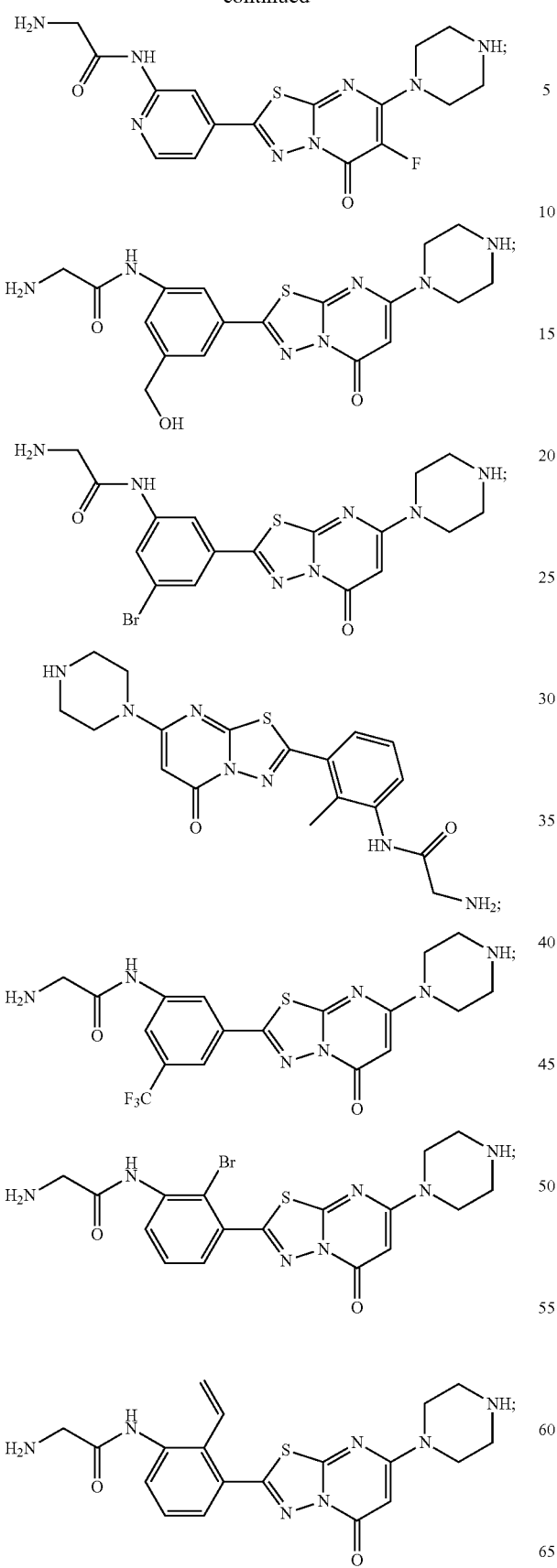
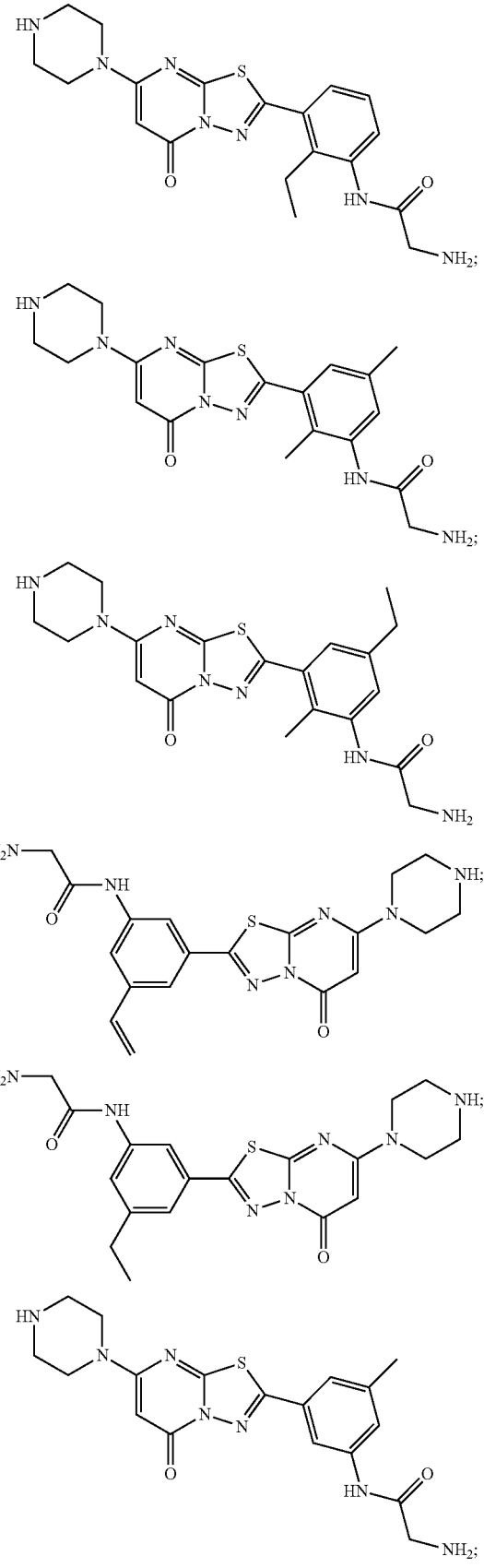

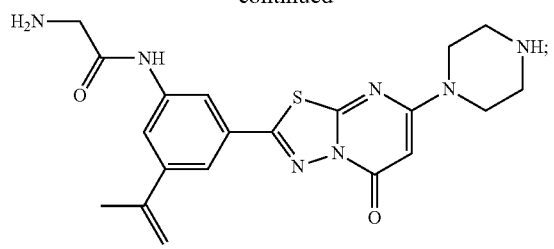
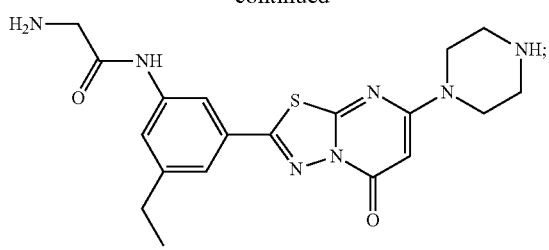
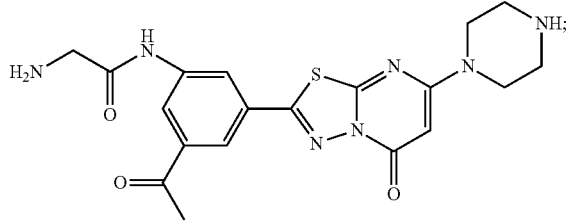
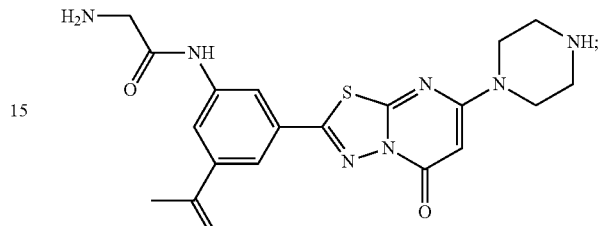
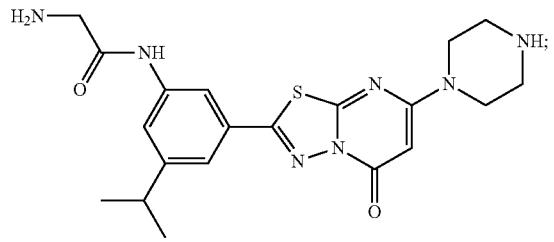
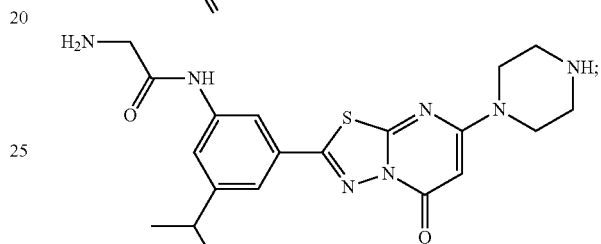
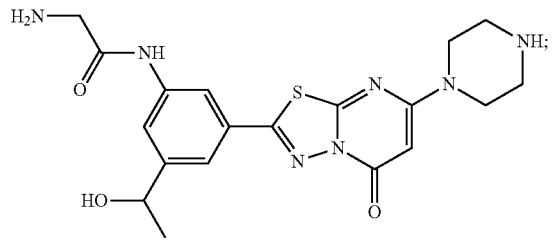
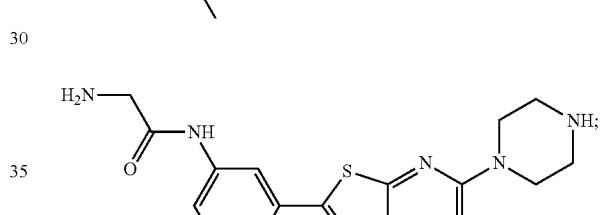
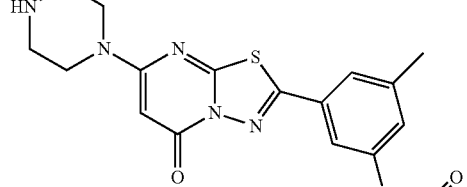
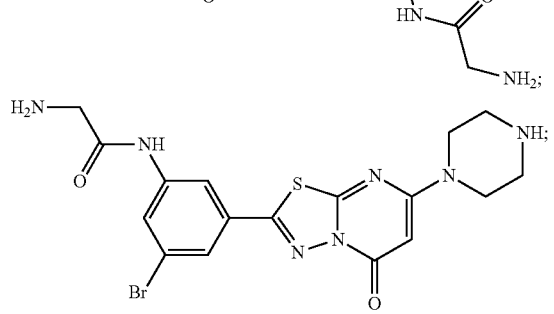
1.40. the compound of Formula P, wherein said compound is selected from:
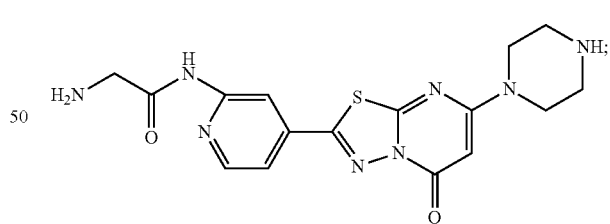
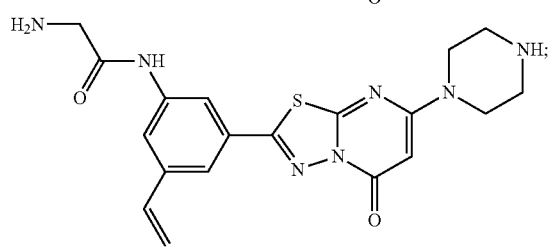
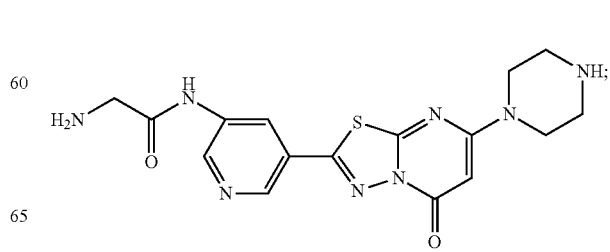

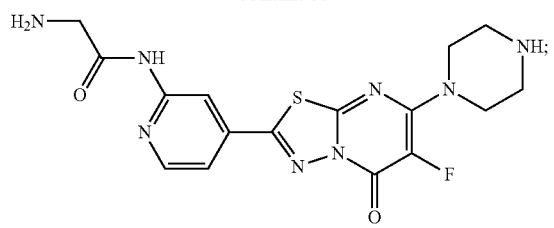
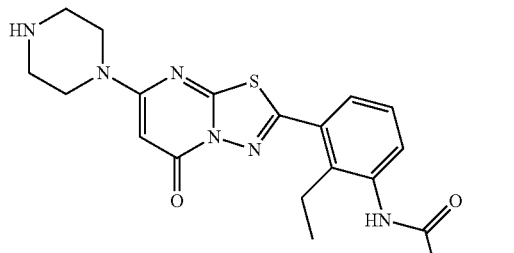
1.41. the compound of Formula I, wherein said compound is selected from:
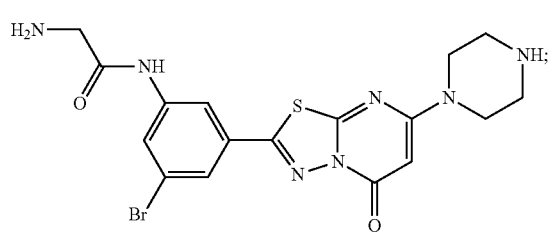
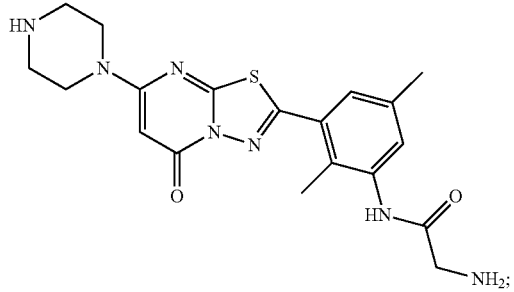
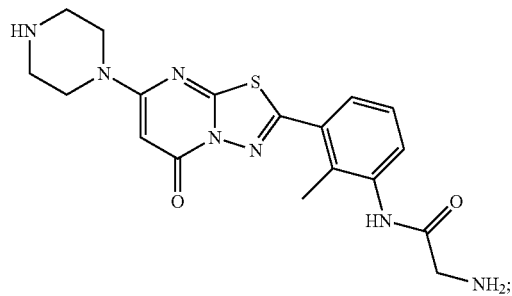
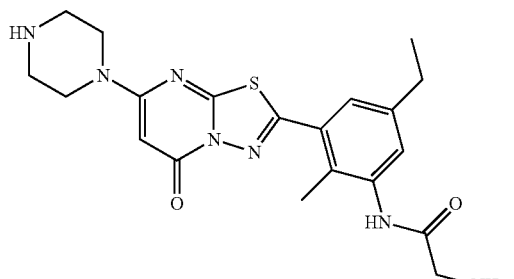
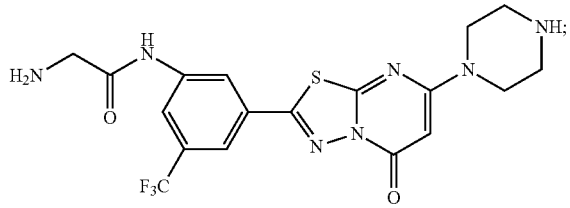
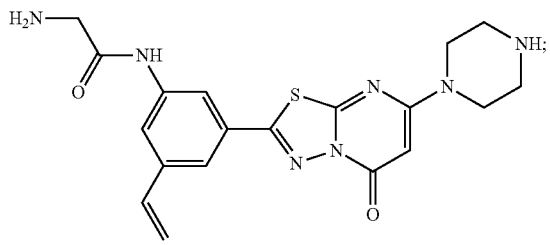
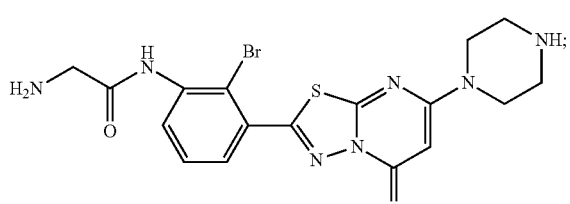
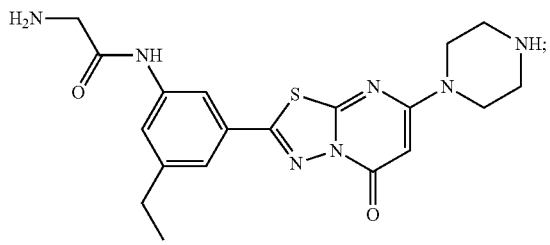
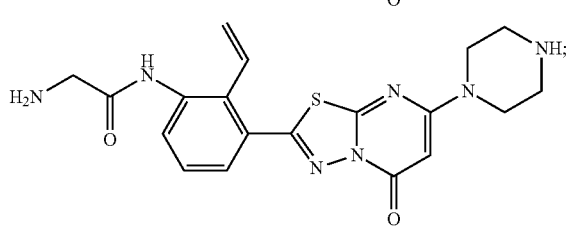
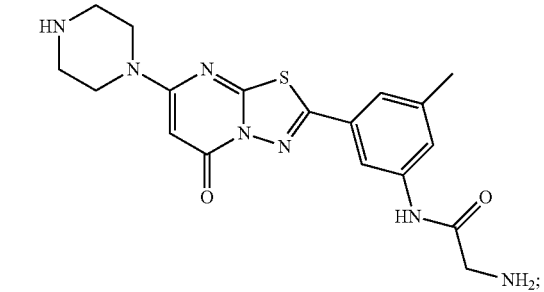

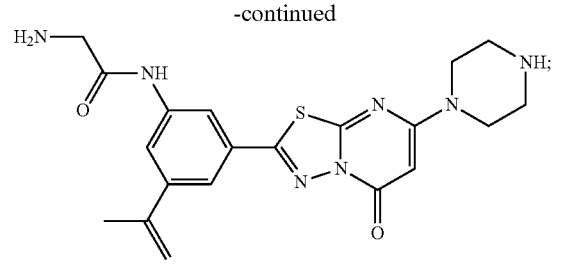
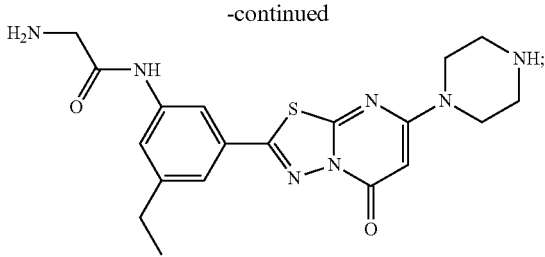
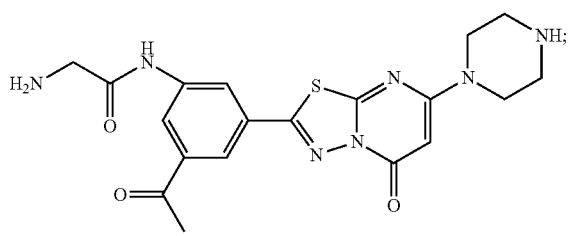
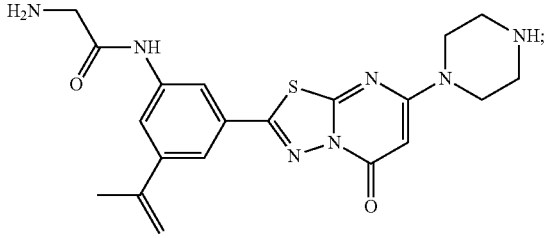
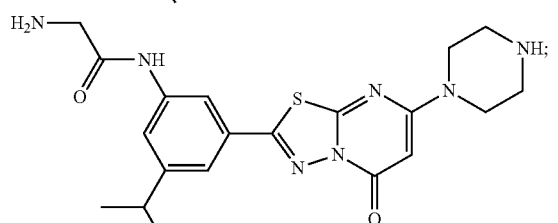
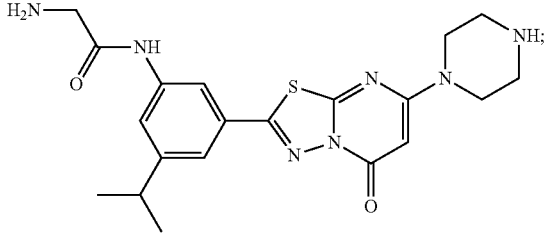
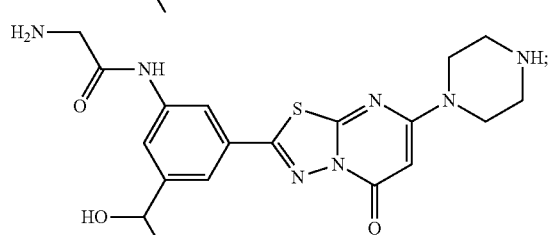
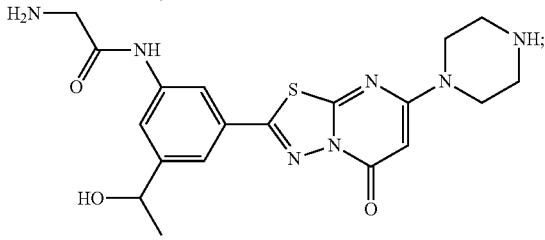
1.42. the compound of Formula I, wherein said compound is selected from:
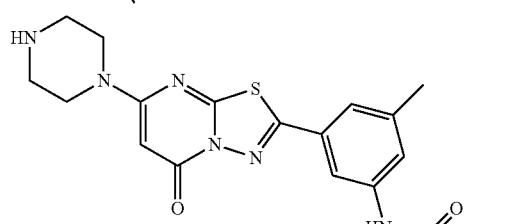
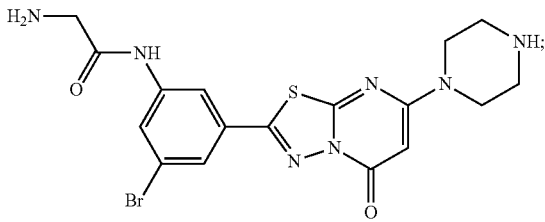
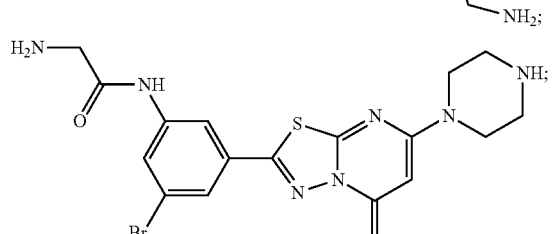
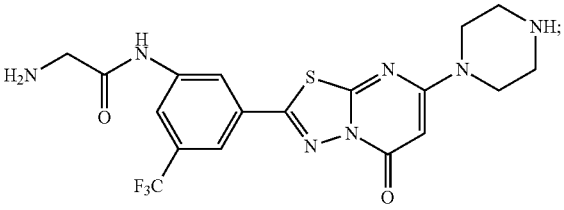
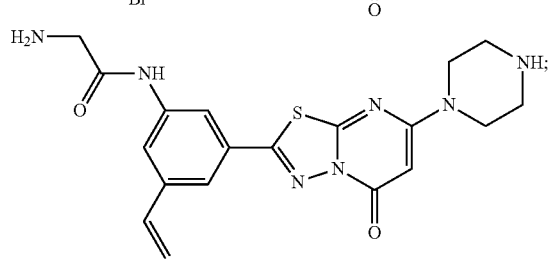
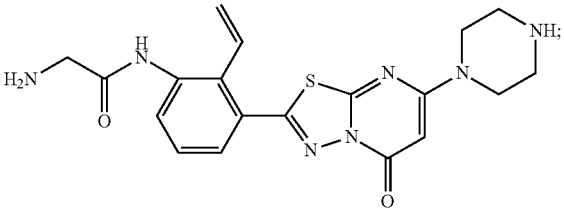

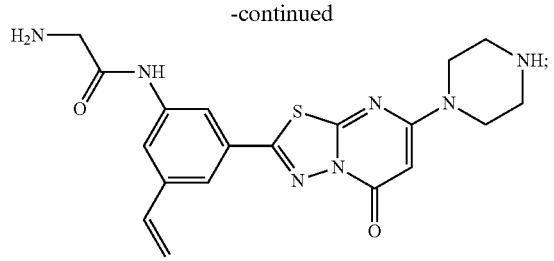
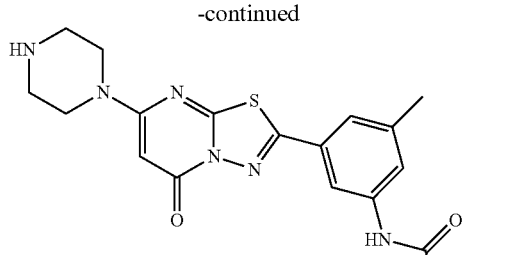
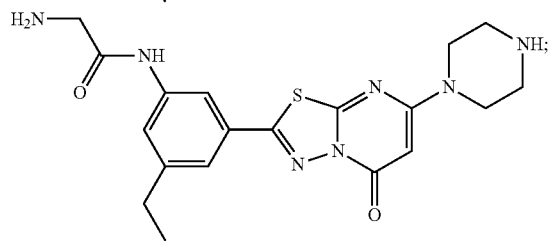
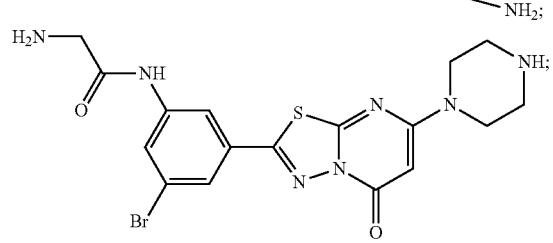
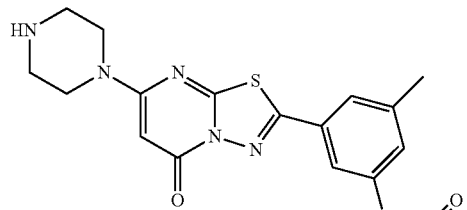
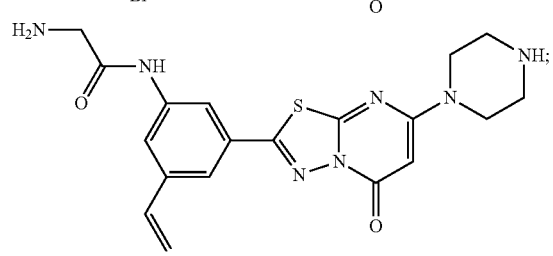
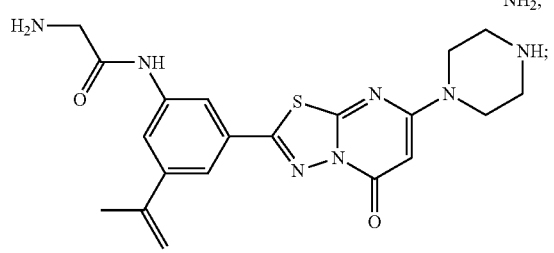
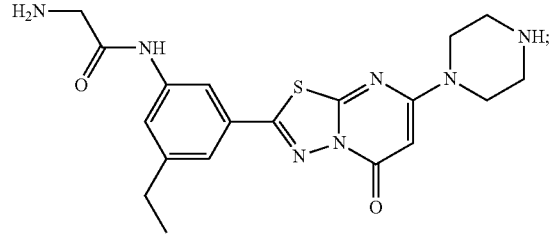
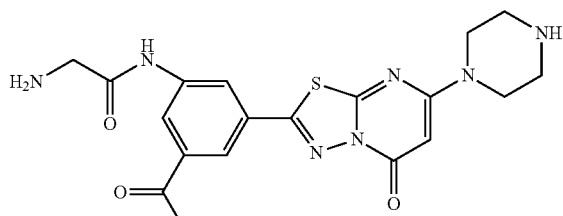
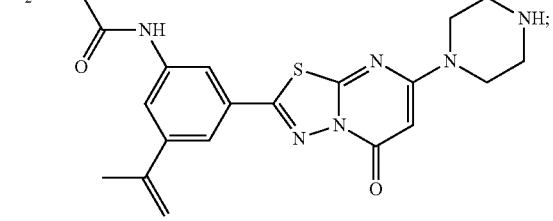
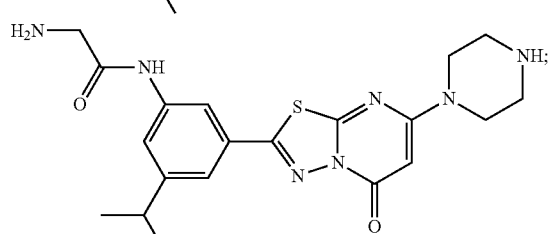
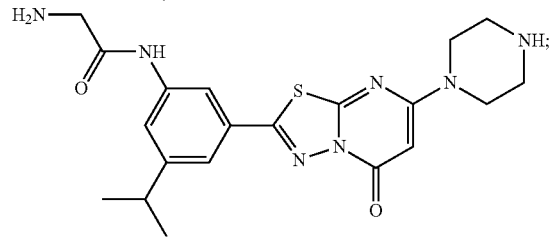
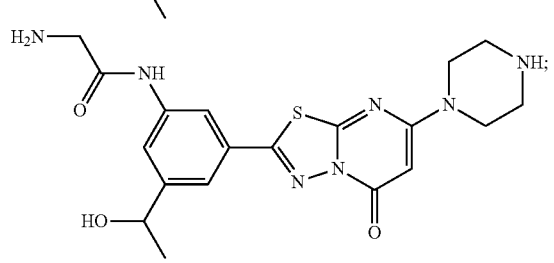
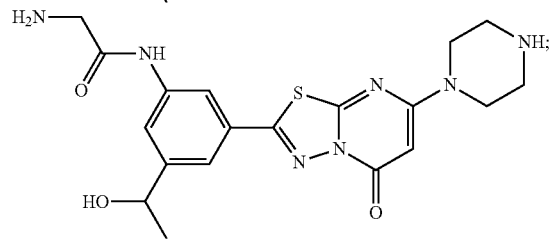

1.43. the compound according to any of the preceding formulae wherein said compound has an $IC_{50}$ value of less than 100 μM, in an aggregation assay as described in Example 15 and/or a percentage of inhibition of greater than 30%, at a concentration of 100 μM or less in an adhesion assay as described in Example 15;

in free or salt form.

In another embodiment of the first aspect, the invention provides a compound of Formula P-II:

Formula P-II

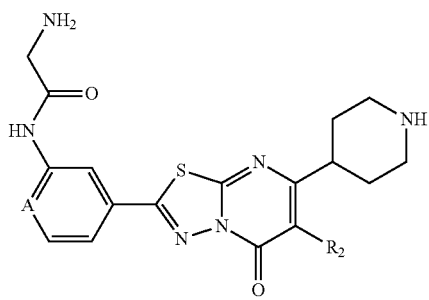

wherein:

A is carbon or nitrogen;

$R_2$ is H or halo (e.g., fluoro);

in free or salt form.

In a further embodiment, the compound of Formula P-II is a compound of Formula II:

Formula II

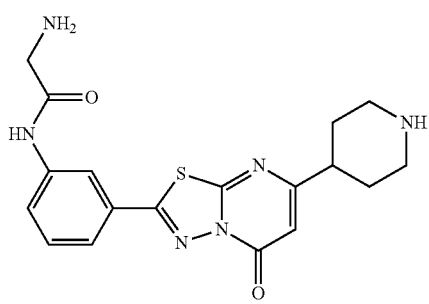

in free or salt form.

In still a further embodiment, the compound of Formula P-II is the following compound:

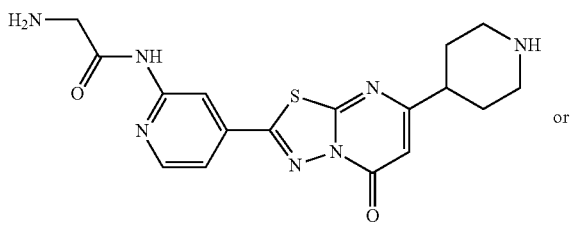

or

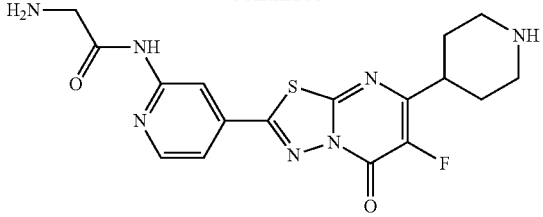

in free or salt form.

In yet another further embodiment, the invention provides the compound according to Formula P-II or Formula II, wherein said compound has an $IC_{50}$ value of less than 100 μM, in an aggregation assay as described in Example 15 and/or a percentage of inhibition of greater than 30%, at a concentration of 100 μM or less in an adhesion assay as described in Example 15, in free or salt form.

In the second aspect, the invention provides a Pharmaceutical Composition comprising the Compound of Formula P, or any of 1.1-1.43, in free or pharmaceutically acceptable salt form, in combination or association with a pharmaceutically acceptable diluent or carrier (Pharmaceutical Composition P). In another embodiment of the second aspect, the invention provides a Pharmaceutical Composition comprising the Compound of Formula I, or any of 1.1-1.27, 1.41-1.43, in free or pharmaceutically acceptable salt form, in combination or association with a pharmaceutically acceptable diluent or carrier (Pharmaceutical Composition I). In still another embodiment of the second aspect, the invention provides a Pharmaceutical Composition comprising the Compound of Formula P-II, in free or pharmaceutically acceptable salt form, in combination or association with a pharmaceutically acceptable diluent or carrier (Pharmaceutical Composition P-II). In a further embodiment, the Pharmaceutical Composition P-II comprises the compound of Formula II, in free or pharmaceutically acceptable salt form (Pharmaceutical Composition II). The Pharmaceutical Compositions of the Invention as hereinbefore described are useful, e.g., for preventing or inhibiting platelet adhesion and/or aggregation in treating thrombotic a disorder in a subject in need thereof. In yet another embodiment, the invention provides the Pharmaceutical Compositions of the Invention as hereinbefore described useful for inhibiting or reducing platelet aggregation and/or adhesion.

In the third aspect, the invention provides a method for inhibiting or reducing platelet aggregation and/or adhesion comprising administering to a subject in need thereof, an effective amount of the Compound of Formula P, any of 1.1-1.43, in free or pharmaceutically acceptable salt form, such that platelet aggregation and/or adhesion is reduced (Method P). In a further embodiment of the third aspect, the invention provides a method for inhibiting or reducing platelet aggregation and/or adhesion comprising administering to a subject in need thereof, an effective amount of the Compound of Formula I, or any of 1.1-1.27, 1.41-1.43, in free or pharmaceutically acceptable salt form, such that platelet aggregation and/or adhesion is reduced (Method I). In still another embodiment of the third aspect, the invention provides a method for inhibiting or reducing platelet aggregation and/or adhesion comprising administering to a subject in need thereof, an effective amount of a Compound of Formula P-II, in free or pharmaceutically acceptable salt form, such that platelet aggregation and/or adhesion is reduced (Method P-II). In a further embodiment, Method P-II comprises administering to a subject in need thereof, an effective amount of a Compound of Formula II (Method II), in free or pharmaceutically acceptable salt form.

In a further embodiment of the third aspect, the invention provides Method P, I, P-II or II, wherein reduction of platelet aggregation and/or adhesion treats or prevent a thrombotic disorder, e.g. selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

In the fourth aspect, the invention provides a method for the treatment or prophylaxis of a thrombotic disorder comprising administering to a subject at risk of a thrombotic disorder, an effective amount of the Compound of Formula P, or any of 1.1-1.43, in free or pharmaceutically acceptable salt form, such that platelet aggregation and/or adhesion is reduced (Method P-III). In a further embodiment, the invention provides a method for the treatment or prophylaxis of a thrombotic disorder comprising administering to a subject at risk of a thrombotic disorder, an effective amount of the Compound of Formula I, or any of 1.1-1.27, 1.41-1.43, in free or pharmaceutically acceptable salt form, such that platelet aggregation and/or adhesion is reduced (Method III). In another embodiment of the fourth aspect, the invention provides a method for the treatment or prophylaxis of a thrombotic disorder comprising administering to a subject at risk of a thrombotic disorder, an effective amount of the Compound of Formula P-II, in free or pharmaceutically acceptable salt form, such that platelet aggregation and/or adhesion is reduced (Method P-IV). In a further embodiment, Method P-IV comprises administering to a subject at risk of a thrombotic disorder, an effective amount of the Compound of Formula P-II, in free or pharmaceutically acceptable salt form (Method IV).

The invention further provides for the following methods:

7.1 Method P-III, III, P-IV or IV, wherein said thrombotic disorder is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation;

7.2 Method P-III, III, P-IV or IV, wherein said thrombotic disorder is thrombosis as a result of angioplasty or stent placement;

7.3 Method P-III, III, P-IV or IV, wherein subject at risk of thrombotic disorder is a subject who has a history of vascular surgery;

7.4 Method P-III, III, P-IV or IV, or any of Methods 7.1-7.3, further comprises administering to said subject an effective amount of at least one therapeutic agent selected from a group consisting of anti-coagulant, anti-platelet, and thrombolytic agents in conjunction with the Compound P, I, P-II or II of the current invention as hereinbefore described, in free or pharmaceutically acceptable salt form;

7.5 Method P-III, III, P-IV or IV or any of Methods 7.1-7.4, further comprises administering to said subject an effective amount of at least one therapeutic agent selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, reta-plase, tenecteplase, prasugrel, aspirin, ticlopidine, clopidogrel, ticagrelor, abciximab, eptifibatide and tirofiban in conjunction with the Compound P, I, P-II or II of the current invention as hereinbefore described, in free or pharmaceutically acceptable salt form;

7.6 Method P-III, III, P-IV or IV or any of Methods 7.1-7.4, further comprises administering to said subject an anti-coagulant or thrombolytic agent in conjunction with the Compound P, I, P-II or II of the current invention as hereinbefore described, in free or pharmaceutically acceptable salt form;

7.7 Method P-III, III, P-IV or IV or any of Methods 7.1-7.4, further comprises administering to said subject an effective amount of heparin in conjunction with the Compound P, I, P-II or II of the current invention as hereinbefore described, in free or pharmaceutically acceptable salt form.

The invention further provides any of the foregoing methods wherein the compounds of the present invention (a) reduce platelet inhibition with a percentage of inhibition of greater than 30%, preferably greater than 50% at a concentration of 100 µM or less; and/or (b) reduce platelet aggregation, e.g., with an $IC_{50}$ of less than 100 µM, preferably less than 25 µM in an ADP or other agonist-induced platelet aggregation assay and/or in a fibrinogen binding assay as described in the examples below.

In a particular embodiment, the invention is a method for the treatment or prophylaxis of a thrombotic disorder comprising administering heparin in conjunction with the Compound of Formula P, I, P-II or II of the current invention as hereinbefore described, in free or pharmaceutically acceptable salt form, particularly the Compound of Formula P of Formula I, in free or pharmaceutically acceptable salt form.

Without being bound to any theory, it is believed that binding of ligand by the receptor induces conformational changes in $\alpha IIb\beta 3$, exposing the ligand-induced binding sites (LIBS). With traditional $\alpha IIb\beta 3$-inhibitors such as tirofiban and eptifibatide, binding of these compounds to both the $\alpha IIb$ and to the divalent cation in the $\beta 3$ subunit's metal ion dependant adhesion site (MIDAS) inhibits platelet adhesion. It is believed, however, that the interaction with the $\beta 3$ subunit's metal ion dependant adhesion site (MIDAS) is likely to be responsible for initiating the conformational change which results in both the thrombocytopenia and the increased mortality rate of traditional $\alpha IIb\beta 3$ antagonists. The present invention identifies $\alpha IIb\beta 3$ inhibitors that are capable of inhibiting fibrinogen binding without inducing the binding of one more integrin $\beta 3$ LIBS-specific mAbs. Therefore, in one embodiment, the Compounds of the Invention e.g., the Compound of Formula P, I, P-II or II in free or salt form may bind to $\alpha IIb$, and in some cases induce $\alpha IIb$ LIBS exposure, without inducing $\beta 3$ LIBS exposure. Such compounds thus demonstrate specific binding to $\alpha IIb\beta 3$ integrin and inhibition of platelet adhesion without the disadvantage of inducing the change in conformation of the $\beta 3$ and consequent risk of complications following dissociation of the compounds from the $\alpha IIb\beta 3$.

In the fifth aspect, the invention provides a drug-eluting stent wherein the drug or drugs eluted comprise the Compound of Formula P, or any of 1.1-1.43, in free or pharmaceutically acceptable salt form as hereinbefore described. In a further embodiment of the fifth aspect, the invention provides a drug-eluting stent wherein the drug or drugs eluted comprise the Compound of Formula I, or any of 1.1-1.27, 1.41-1.43, in free or pharmaceutically acceptable salt form as hereinbefore described. In another embodiment of the fifth aspect, the invention provides a drug-eluting stent wherein the drug or drugs eluted comprise the compound of Formula P-II or Formula II, in free or pharmaceutically acceptale salt form as hereinbefore described. For example, the invention provides a stent, e.g., an arterial stent, for example a coronary artery or carotid artery stent, which comprises a biocompatible polymer matrix which comprises or is associated with the Compound of Formula P, I, P-II or II, in free or pharmaceutically acceptable salt form as hereinbefore described. The stent may be made of metal, plastic, biodegradable or bioabsorbable material or combination thereof, e.g., stainless steel, nickel-titanium alloy, colbalt-alloy, tantalum, silicone, polytetrafluoroethylene, magnesium alloy or poly-L-lactide. For example, a stent may be a metallic stent (e.g., stainless steel, nickel-titanium alloy, colbalt alloy, or tantalum) partially or wholly coated with a biocompatible polymer, e.g., a plastic (e.g., polytetrafluoroethylene) or a polymeric carrier (e.g., phosphorylcholine or polylactic acid) which polymer comprises or is associated with the Compound P, I, P-II or II, in free or pharmaceutically acceptable salt form as hereinbefore described, e.g., such that said Compound is presented or released in a manner and amount effective to inhibit platelet adhesion and/or aggregation in the vicinity of the stent. The stent may further comprise or be associated with an additional drug or drugs, e.g., an antiproliferative agent, e.g., sirolimus, everolimus, zotarolimus, tacrolimus, or paclitaxel, and/or an anticoagulant, e.g., heparin.

In the sixth aspect, the invention provides the Compound of Formula P, or any of 1.1-1.43, in free or pharmaceutically acceptable salt form as hereinbefore described, for use as a pharmaceutical, e.g. use of the Compound of Formula P, or any of 1.1-1.43, in free or pharmaceutically acceptable salt form as hereinbefore described, e.g., (in the manufacture of a medicament) for the treatment or prophylaxis of a thrombotic disorder, e.g., according to any of Methods P, P-III or any of methods 7.1-7.7. In a further embodiment of the sixth aspect, the invention provides the Compound of Formula I, or any of 1.1-1.27, 1.41-1.43, in free or pharmaceutically acceptable salt form as hereinbefore described, for use as a pharmaceutical, e.g. use of the Compound of Formula I, or any of 1.1-1.27, 1.41-1.43, in free or pharmaceutically acceptable salt form as hereinbefore described, e.g., (in the manufacture of a medicament) for the treatment or prophylaxis of a thrombotic disorder, e.g., according to any of Methods I, III or any of methods 7.1-7.7. In another embodiment of the sixth aspect, the invention provides the Compound of Formula P-II or Formula II, in free or pharmaceutically acceptable salt form, e.g., (in the manufacture of a medicament) for the treatment or prophylaxis of a thrombotic disorder, e.g., according to any of methods P-II, II, P-IV, IV or any of methods 7.1-7.7.

In the seventh aspect, the invention provides a Pharmaceutical Composition comprising the Compound of Formula P, or any of 1.1-1.43, in free or pharmaceutically acceptable salt form as hereinbefore described, for use as a pharmaceutical e.g., (in the manufacture of a medicament) for the treatment or prophylaxis of a thrombotic disorder, e.g., according to any of Methods P, P-III, or any of methods 7.1-7.7. In a further embodiment of the seventh aspect, the invention provides a Pharmaceutical Composition comprising the Compound of Formula I, or any of 1.1-1.27, 1.41-1.43, in free or pharmaceutically acceptable salt form as hereinbefore described, for use as a pharmaceutical e.g., (in the manufacture of a medicament) for the treatment or prophylaxis of a thrombotic disorder, e.g., according to any of Methods I, III or any of methods 7.1-7.7. In still another embodiment of the seventh aspect, the invention provides a Pharmaceutical Composition comprising the Compound of Formula P-II or Formula II, in free or pharmaceutically acceptable salt form as hereinbefore described, for use as a pharmaceutical e.g., (in the manufacture of a medicament) for the treatment or prophylaxis of a thrombotic disorder, e.g., according to any of Methods P-II, II, P-IV, IV or any of methods 7.1-7.7.

DETAILED DESCRIPTION OF THE INVENTION

As used herein, the term "αIIbβ3" or "integrin αIIbβ3" refers to the receptor on the surface of human platelets. It is a heterodimeric complex composed of both αIIb and β3 subunits responsible for binding adhesive plasma proteins, most notably fibrinogen and von Willebrand factor.

The term "antagonist" refers to any ligand or molecule that binds to receptors and competitively or noncompetitively blocks the binding of ligand to that receptor. Therefore, "αIIbβ3 antagonist" refers to any ligand or molecule that competitively or noncompetitively blocks αIIbβ3.

"LIBS" refers to ligand-induced binding sites on αIIbβ3 that are presented or exposed upon the binding of a ligand or antagonist by the receptor.

"LIBS-specific mAbs" refers to monoclonal antibodies that bind to the exposed ligand-induced binding sites of αIIbβ3. Examples of LIBS-specific mAbs include AP5, PMI-1 and LIBS1.

The term "thrombotic disorders" refers to disorders characterized by formation of a thrombus that obstructs vascular blood flow. Examples of thrombotic disorders include stroke, myocardial infarction, stable or unstable angina, peripheral vascular disease, abrupt closure following angioplasty or stent placement and thrombosis induced by vascular surgery. Thrombotic disorders also include disorders characterized by formation of a thrombus caused by atrial fibrillation or inflammation.

The phrase "subject at risk of thrombotic disorders" or "subject in need thereof" includes subjects who have a history of vascular intervention (e.g. angioplasty, stent placement, aortocoronary bypass or insertion of prosthetic heart valves), cardiovascular abnormality (e.g. atrial fibrillation) or a family history of vascular diseases (e.g., coronary artery disease (CAD), systemic hypertension, diabetes mellitus, hyperlipidemia, bicuspid aortic valve, hypertrophic cardiomyopathy or mitral valve prolapse). The term "subject" may include human or non-human (e.g., an animal).

The term "platelet adhesion" refers to the binding of platelet membrane proteins to fibrinogen, collagen, von Willebrand factor (vWF) or other adhesive glycoproteins (e.g., fibronectin, laminin).

The term "platelet aggregation" refers to the attachment of activated platelets one to another, which results in the formation of aggregates or clumps of activated platelets.

The phrase "inhibit or reduce platelet adhesion and/or aggregation" is intended to mean at least a 30% inhibition of platelet activity at a concentration of 100 μM or lower in a given assay, relative to platelet activity in the absence of the compound.

The phrase "antagonist known to expose β3 LIBS" herein refers to agents that induce conformational in β3, for example tirofiban.

The term "anticoagulants" herein refers to any compound or substance that either stimulates natural inhibitor of coagulant proteases or blocks the coagulation cascade. Examples of anticoagulants include, but are not limited to heparin, warfarin, phenprocoumon, fondaparinux, lepirudin, bivalirudin, argatroban, danaparoid and drotrecogin alfa.

The term "anti-platelet agents" herein refers to compound or substance that prevents platelet adhesion and/or aggregation. Examples of anti-platelet agents include, but are not limited to prasugrel, aspirin, ticlopidine, clopidogrel, ticagrelor, abciximab, eptifibatide and tirofiban.

The term "fibrinolytic agents" therefore refers to any compound or substance that lyses pathological thrombi. "Thrombolytic agents" are agents that are fibrinolytic, i.e., agents that convert plasminogen to plasmin, which lyses fibrin. Examples of fibrinolytic agents include but are not limited to streptokinase and tissue plasminogen activator (t-PA).

The term "stent" herein refers to expandable wire form or perforated tube that is inserted into a natural conduit of the body, such as an artery, usually a coronary artery, to prevent or counteract a disease-induced localized flow constriction.

The term "optionally substituted" is intended to mean substituted with the substituents defined or unsubstituted. For example, phenyl optionally substituted with one or more nitro means in some instances, the phenyl is substituted with one or more nitro groups and in other instances, the phenyl is unsubstituted.

The binding of LIBS-specific mAbs to αIIbβ3 may be measured by comparing the binding of LIBS-specific mAbs to αIIbβ3 in the presence of testing compound with the binding of LIBS-specific mAbs to αIIbβ3 in the absence or presence of a control such as untreated platelets and/or other known αIIbβ3 inhibitors that are known to cause β3 LIBS exposure, e.g., tirofiban. For example, the test compound may bind to faith and optionally increases binding of at least one αIIb LIBS-specific mAb relative to binding to unactivated platelets without increasing the binding of one or more β3 LIBS-specific mAbs relative to binding to unactivated platelets and/or produces less binding relative to binding in the presence of an agent known to bind to and directly activate αIIbβ3 so as to expose β3 LIBS.

As used herein, the term "alkyl" or "alkyl chain" or "alkylene" refers to a linear or branched, saturated or unsaturated, aliphatic hydrocarbon. Unless otherwise specified, alkyl refers to a hydrocarbon chain containing one to four carbon atoms. Examples of alkyl may include, but are not limited to methyl, ethyl, tert-butyl and the like as well as alkenyl or alkynyl substituents.

The term "$C_3$-$C_{10}$cycloalky" or "$C_{3-10}$cycloalky" refers to fully or partially saturated, carbocyclic, non-aromatic hydrocarbon radicals having three to eight carbon atoms. Examples of $C_3$-$C_{10}$cycloalkyl optionally containing one or more heteroatoms selected from a group consisting of O or N include, but are not limited to, cyclopropyl, cyclobutyl, cyclopentyl, cyclopentenyl, cyclohexyl or cyclohexenyl, piperidinyl, piperazinyl, morpholinyl, imidazolinyl, pyrrolidinyl. These cycloalkyl systems may be attached via the heteroatom or any other carbon on the system. $C_3$-$C_{10}$cycloalky may also refer to non-aromatic cyclic system fused to an aromatic cyclic system. An example of this includes tetrahydroquinolinyl.

The term "aryl" refers to any aromatic ring system. Aromatic compounds include phenyl, naphthyl and their derivatives.

The term "heteroaryl" is intended to mean a stable 5- to 6-membered monocyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to another ring.

The term "acyl" is intended to encompass R—C(O)— wherein R is $C_{1-4}$alkyl, wherein said alkyl is optionally substituted with one or more halo, hydroxy, or $C_{1-4}$alkoxy. One example of acyl is $CH_3$—C(O)—.

The Compounds of the Invention may comprise one or more chiral carbon atoms. The compounds thus exist in individual isomeric, e.g., enantiomeric or diasteriomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diasteromeric mixtures) thereof. Accordingly, the Compound of the Invention may be a racemic mixture or it may be predominantly, e.g., in pure, or substantially pure, isomeric form, e.g., greater than 70% enantiomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like)

Compounds of the Invention may exist in free or salt form, e.g., as acid addition salts (e.g., hydrochloric acid, toluene sulfonic acid, methane sulfonic acid, benzene sulfonic acid, trifluoroacetic acid, and the like). In this specification, unless otherwise indicated language such as Compounds of the Invention is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. In particular embodiment, the salt of the compound of the invention is a trifluoroacetic acid addition salt.

Compounds of the Invention may in some cases also exist in prodrug form. A prodrug form is compound which converts in the body to a Compound of the Invention. For example, when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. For example, wherein the compounds of the invention contains a hydroxy group (e.g., Drug-OH), the prodrug (e.g., Drug-O—C(O)—$CH_3$) may hydrolyze under physiological conditions to yield hydroxy (Drug-OH) on the one hand and acid, e.g., carboxylic acid on the other (e.g., $CH_3COOH$), which are themselves physiologically tolerable at doses to be administered. Similarly, wherein the compounds of the invention contains a carboxylic acid group (e.g., Drug-C(O)OH), its prodrug (e.g., Drug-C(O)—O—$CH_2CH_3$) may hydrolyze under physiological conditions to yield the carboxylic acid (Drug-C(O)OH) on the one hand and alcohol, e.g., ethanol on the other (e.g., $CH_3CH_2OH$), which are themselves physiologically tolerable at doses to be administered. As will be appreciated the term thus embraces conventional pharmaceutical prodrug forms.

Compounds of the present invention may be administered orally or parenterally, including intravenous, intramuscular, intraperitoneal, subcutaneous, transdermal, airway (aerosol), rectal, vaginal and topical (including buccal and sublingual) administration. The compounds useful in the invention may generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Dosages of the compounds of the invention will vary depending upon the condition to be treated or prevented and on the identity of the inhibitor being used. Estimates of effective dosages and in vivo half-lives for the individual compounds encompassed by the invention can be made on the basis of in vivo testing using an animal model, such as the mouse model described herein or an adaptation of such method to larger mammals. Appropriate dosage may range from 0.01 mg to 5000 mg. For example, one appropriate dosage may be 0.01-30 mg/Kg, e.g., 26.5 mg/Kg, e.g., 12 mg/Kg.

In addition to their administration singly, the compounds useful according to the invention can be administered in combination or in conjunction with other known therapeutic agents useful for thrombotic disorders such as anticoagulants (e.g., heparin, warfarin, phenprocoumon, fondaparinux, lepirudin, bivalirudin, argatroban, danaparoid, drotrecogin alfa), fibrinolytic agents (e.g., streptokinase or tissue plasminogen activator (t-PA) or other anti-platelet agents (e.g., prasugrel, aspirin, ticlopidine, clopidogrel, ticagrelor, abciximab, eptifibatide and tirofiban). In any event, the administering physician can adjust the amount and timing of drug administration on the basis of results observed using standard measures of platelet activity known in the art or described herein.

EXAMPLES

Synthesis of Compounds of the Present Invention

The compounds described herein and their pharmaceutically acceptable salts may be made using the methods as described and exemplified herein and by methods similar thereto and by methods known in the chemical art. In addition, the compounds of the invention may be made by using similar methods as those described in PCT/US11/44267. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, reaction may require to be run at elevated temperature, for a longer or shorter period of time or in the presence of an acid or base. It is understood by one skilled in the art of organic synthesis that functionality present on various portions of the molecule must be compatible with the reagents and reactions proposed. If not commercially available, starting materials for these processes may be made by procedures, which are selected from the chemical art using techniques similar or analogous to the synthesis of known compounds. Significances of the substituents are as set forth in the formulae hereinbefore defined unless otherwise specified. All references cited herein are hereby incorporated in their entirety by reference.

General Synthetic Procedures.

The synthesis methods described above and/or the following general procedures are used to synthesize compounds having different but analogous structures.

TERMS AND ABBREVIATIONS

ACN=acetonitrile,
Boc-Gly-OH=N-(tert-Butoxycarbonyl)glycine,
Boc-Gly-$NH_2$32 tert-butyl(2-amino-2-oxoethyl)carbamate,
t-BuOH32 tert-butanol,
DCM=dichloromethane,
DMF=N,N-dimethylforamide,
DIPEA=diisopropylethylamine,
DMSO=dimethyl sulfoxide,
EDC=1-ethyl-3-(3-dimethylaminopropyl) carbodiimide,
EtOAc=ethyl acetate,
h=hour(s),
HATU=(2-(7-Aza-1H-benzotriazole-1-yl)-1,1,3,3-tetramethyluronium, hexafluorophosphate,
HCl=hydrochloric acid,
HPLC=high performance liquid chromatography,
Hunig's base=N,N-diisopropylethylamine,
$K_2CO_3$=potassium carbonate,
m=multiplet,
min=minute(s),
MeOH=methanol,
MeCN=acetonitrile,
$MgSO_4$=magnesium sulfate,
$NaIO_4$=Sodium periodate,
$NaHCO_3$=sodium bicarbonate,
$Na_2SO_4$=sodium sulfate,
$Na_2S_2O_4$=sodium dithionite,
$NH_4Cl$=ammonium chloride,
NMO=N-Methylmorpholine-N-oxide,
NMR=nuclear magnetic resonance,
$OsO_4$=osmium tetraoxide,
p=pentet,
PPA=Polyphosphoric acid,
Pd/C=palladium on carbon,
$POCl_3$=phosphorous oxychloride,
Pd($PPh_3$)$_4$=Palladium-tetrakis(triphenylphosphine),
$^i$-$Pr_2$Et=diisopropylethylamine,
rt=room temperature,
s=singlet,
t=triplet,
TFA=trifluoroacetic acid,
THF=tetrahydrofuran,
TLC=thin layer chromatography,
Xantphos=4,5-Bis(diphenylphosphino)-9,9-dimethylxanthene.

$^1$H NMR spectra are recorded on Varian 400 MHz spectrometers. Chemical Shifts are reported in ppm with DMSO-$d_6$ as reference (2.50 ppm). All the analogues analyzed by NMR are TFA salt. Samples are analyzed for purity on an Agilent 1200 series LC/MS equipped with a Luna C18 (3 micron, 3×75 mm) reverse phase column having a flow rate of 0.8 mL/min. The mobile phase is a mixture of acetonitrile containing 0.025% trifluoroacetic acid (TFA) and $H_2O$ containing 0.05% trifluoroacetic acid, respectively. Method: Gradient of 4% to 100% acetonitrile over 7 minutes with flow rate of 0.8 ml/min. All of the analogues for assay have purity greater than 95% based on LC/MS. High resolution mass spectrometry is recorded on Agilent 6210 Time-of-Flight (TOF) LC/MS system.

Example 1

The compound of Example 1 is prepared as described as described or similarly described in the procedures below:

Scheme 1:

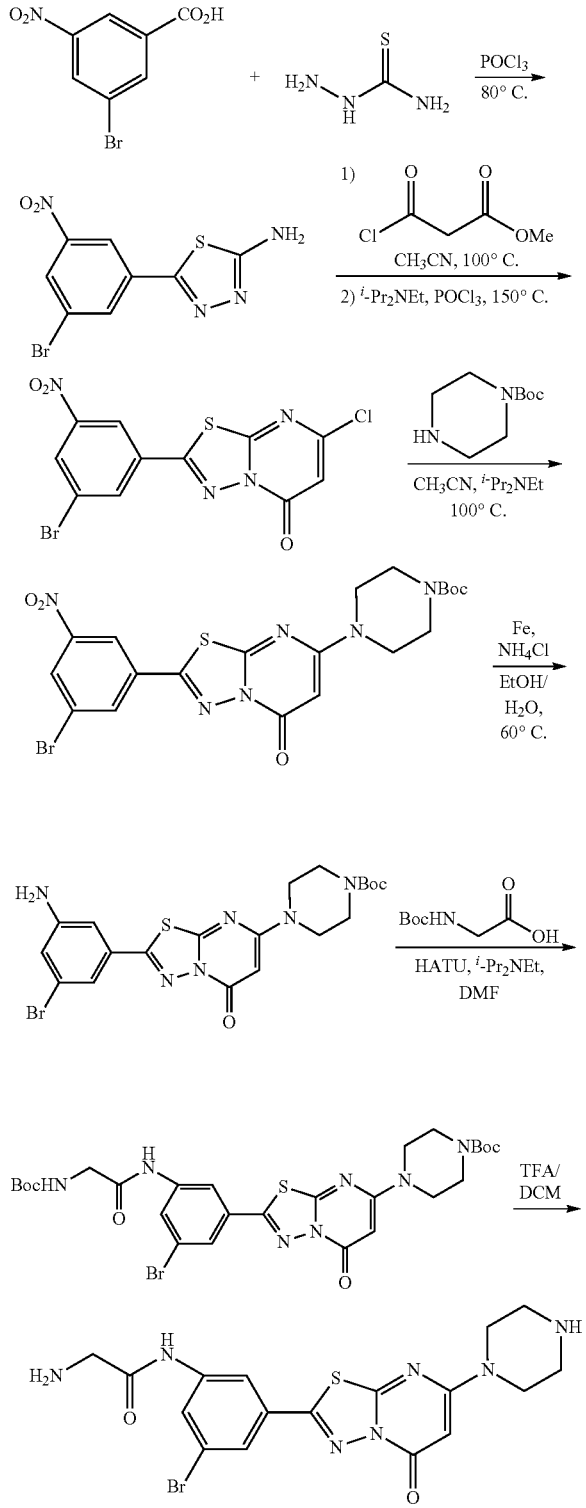

2-amino-N-(3-bromo-5-(5-oxo-7-(piperazin-1-yl)-5H-[1,3,4]thiadiazolo[3,2-a]pyrimidin-2-yl)phenyl)acetamide

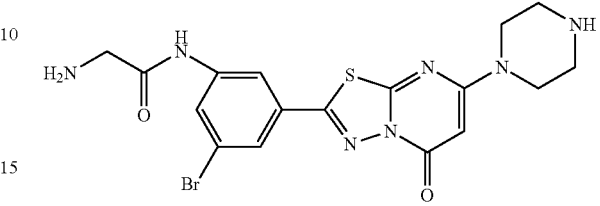

Step 1:

To a solid mixture of 3-bromo-5-nitrobenzoic acid (660 mg, 2.68 mmol) and hydrazinecarbothioamide (244 mg, 2.68 mmol) is added $POCl_3$ (0.500 ml, 5.37 mmol) dropwise with ice/water cooling. The mixture is heated at 80° C. for 3 h. After cooling to room temperature, some EtOAc is added to the sticky mixture which is slowly transferred to ice water. Saturated aqueous $NaHCO_3$ solution is added to adjust pH=9 and the yellow precipitate is filtered, washed first with water then with EtOAc to give the desired product (580 mg, 72%).

Step 2:

To a solution of 5-(3-bromo-5-nitrophenyl)-1,3,4-thiadiazol-2-amine (0.550 g, 1.827 mmol) in $CH_3CN$ (15 ml) is added methyl 3-chloro-3-oxopropanoate (0.235 ml, 2.192 mmol). The mixture is microwaved at 100° C. for 12 min. After cooling to room temperature, $POCl_3$ (5.96 ml, 63.9 mmol) and $^i\text{-}Pr_2NEt$ (0.319 ml, 1.827 mmol) is added and the mixture is microwaved at 150° C. for 30 min. After cooling to room temperature, excess $POCl_3$ and $CH_3CN$ are removed in vacuo and the residue is dissolved in DCM and poured into ice. The DCM solution is washed with saturated aqueous $NaHCO_3$ solution. The organic and aqueous layers filtered through Celite and the organic layer is separated. The organic layer is washed with brine, dried over $Na_2SO_4$. After the removal of organic solvent in vacuo, the crude residue is purified by Biotage column chromatography (EtOAc/DCM: 1/100 to 1/20 gradient) to give the desired product (250 mg, 35%) as a yellow solid.

Step 3:

To a mixture of 2-(3-bromo-5-nitrophenyl)-7-chloro-5H-[1,3,4]thiadiazolo[3,2-a]pyridin-5-one (312 mg, 0.81 mmol) and tert-butyl piperazine-1-carboxylate (180 mg, 0.968 mmol) in $CH_3CN$ (6 ml) is added $^i\text{-}Pr_2NEt$ (0.21 ml, 1.21 mmol) and the mixture is microwaved at 100° C. for 2 h. After cooling to room temperature, solid starts to precipitate out. The solid is filtered and washed with EtOAc and collected. The filtrate is concentrated in vacuo and the crude residue is purified by Biotage column chromatography (MeOH/DCM: 1/100 to 1/20 gradient) to give another portion of product. The total amount of desired product is 355 mg (82%).

Step 4:

To a suspension of tert-butyl 4-(2-(3-bromo-5-nitrophenyl)-5-oxo-5H-[1,3,4]thiadiazolo[3,2-a]pyrimidin-7-yl)piperazine-1-carboxylate (460 mg, 0.86 mmol) in EtOH (5 ml) and water (1 ml) are added iron powder (239 mg, 4.38 mmol) and $NH_4Cl$ (137 mg, 2.57 mmol) and the mixture is heated at 70° C. for 5 h. After cooling to room temperature, EtOAc (30 ml) is added and the mixture is further stirred for 10 min then filtered through a pad of Celite. The combined filtrate is washed with brine and the organic layer is dried over Na₂SO₄. After the removal of EtOAc in vacuo, the crude residue is purified by Biotage column chromatography (MeOH/DCM: 1/100 to 1/20 gradient) to give the desired product (380 mg, 88%).

Step 5:

To a solution of tert-butyl 4-(2-(3-amino-5-bromophenyl)-5-oxo-5H-[1,3,4]thiadiazolo[3,2-a]pyrimidin-7-yl)piperazine-1-carboxylate (30.0 mg, 0.059 mmol) in DMF (2 ml) are added Boc-Gly-OH (20.7 mg, 0.118 mmol), HATU (45.0 mg, 0.118 mmol) and $^i$-Pr₂NEt (31 μl, 0.177 mmol). The mixture is stirred at room temperature for 2 h. EtOAc (10 ml) is added and the solution is washed with H₂O and brine. The organic layer is dried over Na₂SO₄. After removing EtOAc, the residue is purified by Biotage column chromatography (MeOH/DCM: 1/100 to 1/20 gradient) to give the desired product (33 mg, 84%).

Step 6:

To a solution of tert-butyl 4-(2-(3-bromo-5-(2-(tert-butoxycarbonylamino)-acetamido)phenyl)-5-oxo-5H-[1,3,4]thiadiazolo[3,2-a]pyrimidin-7-yl)piperazine-1-carboxylate (30 mg, 0.045 mmol) in DCM (2 ml) is added TFA (0.5 ml) and the mixture is stirred for 1 h. After the removal of DCM in vacuo, the crude residue is directly purified by preparative HPLC to give the desired product, 2-amino-N-(3-bromo-5-(5-oxo-7-(piperazin-1-yl)-5H-[1,3,4]thiadiazolo[3,2-a]pyrimidin-2-yl)phenyl)acetamide: ¹H NMR (400 MHz, DMSO-d₆) δ 8.70-8.20 (br.s., 3H), 8.19 (t, J=1.8 Hz, 1H), 8.11 (t, J=1.8 Hz, 1H), 7.83 (t, J=1.8 Hz, 1H), 5.61 (s, 1H), 3.84 (s, 2H), 3.79 (t, J=5.2 Hz, 4H), 3.18 (t, J=5.2 Hz, 4H); LC/MS: $t_R$=2.743 min; HRMS: m/z (M+H⁺)=464.0495 and 466.0479 (Calculated for C₁₇H₁₉BrN₇O₂S=464.0499 and 466.0479).

Example 2

2-amino-N-(2-methyl-3-(5-oxo-7-(piperazin-1-yl)-5H-[1,3,4]thiadiazolo[3,2-a]pyrimidin-2-yl)phenyl)acetamide

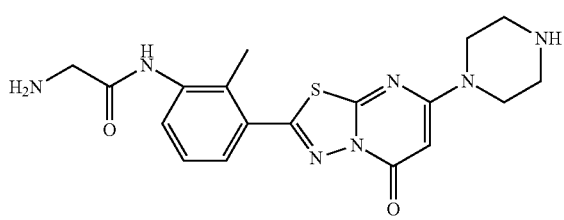 [SMILES: Cc1c(NC(=O)CN)cccc1-c1nn2c(=O)cc(N3CCNCC3)nc2s1]

Using the procedures described or similarly described in Example 1, the compound of Example 2 is prepared except that 2-methyl-3-nitrobenzoic acid is used as starting material in step 1. ¹H NMR (400 MHz, DMSO-d₆) δ 10.18 (s, 1H), 9.20-9.00 (br.s., 2H), 8.35-8.10 (br.s., 3H), 7.62 (dd, J=8.0, 1.2 Hz, 1H), 7.54 (dd, J=8.0, 1.2 Hz, 1H), 7.45 (t, J=8.0 Hz, 1H), 5.63 (s, 1H), 3.90 (s, 2H), 3.80 (t, J=5.0 Hz, 4H), 3.19 (t, J=5.0 Hz, 4H), 2.40 (s, 3H); LC/MS: $t_R$=2.224 min; HRMS: m/z (M+H⁺)=400.1547 (Calculated for C₁₈H₂₂N₇O₂S=400.1556).

Example 3

2-amino-N-(3-(5-oxo-7-(piperazin-1-yl)-5H-[1,3,4]thiadiazolo[3,2-a]pyrimidin-2-yl)-5-(trifluoromethyl)phenyl)acetamide

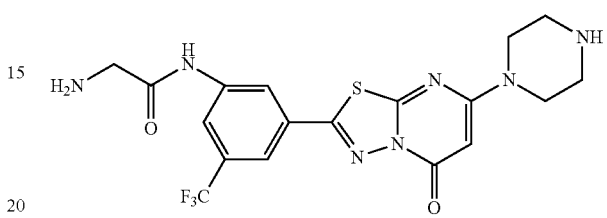

Using the procedures described or similarly described in Example 1, the compound of Example 3 is prepared except that 3-trifluoromethyl-5-nitrobenzoic acid is used as starting material in step 1. ¹H NMR (400 MHz, DMSO-d₆) δ 11.15 (s, 1H), 9.00-8.80 (br.s., 2H), 8.84 (d, J=1.6 Hz, 1H), 8.25 (d, J=1.6 Hz, 1H), 8.30-8.10 (br.s., 3H), 7.93 (t, J=0.8 Hz, 1H), 5.63 (s, 1H), 3.87 (s, 2H), 3.95 (t, J=5.2 Hz, 4H), 3.19 (t, J=5.2 Hz, 4H); LC/MS: $t_R$=2.832 min; HRMS: m/z (M+H⁺)=454.1269 (Calculated for C₁₈H₁₉F₃N₇O₂S=454.1273).

Example 4

2-amino-N-(2-bromo-3-(5-oxo-7-(piperazin-1-yl)-5H-[1,3,4]thiadiazolo[3,2-a]pyrimidin-2-yl)phenyl)acetamide

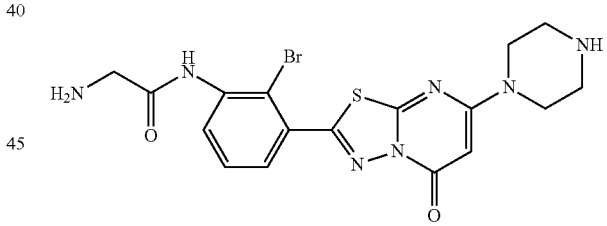

Using the procedures described or similarly described in Example 1, the compound of Example 4 is prepared except 2-bromo-3-nitrobenzoic acid is used as starting material in step 1. The peaks of some protons split into two groups with integration ratio of major/minor 1.7/1. ¹H NMR (400 MHz, DMSO-d₆) δ 7.97 (dd, J=8.0, 1.6 Hz, 1H, minor), 7.88 (dd, J=8.0, 1.6 Hz, 1H, minor), 7.82 (dd, J=8.0, 1.6 Hz, 1H, major), 7.78 (dd, J=8.0, 1.6 Hz, 1H, major), 7.66 (t, J=8.0 Hz, 1H, major), 7.63 (t, J=8.0 Hz, 1H, minor), 5.639 (s, 1H, major), 5.637 (s, 1H, minor), 3.93 (s, 1H, minor), 3.91 (s, 1H, major), 3.81 (t, J=5.2 Hz, 4H), 3.19 (t, J=5.2 Hz, 4H); LC/MS: $t_R$=2.496 min; HRMS: m/z (M+H⁺)=464.0499 and 466.0476 (Calculated for C₁₇H₁₉BrN₇O₂S=464.0499 and 466.0479).

Examples 5-8

The compounds of Examples 5-8 are prepared as described or similarly described in the procedures below:

Scheme 2:

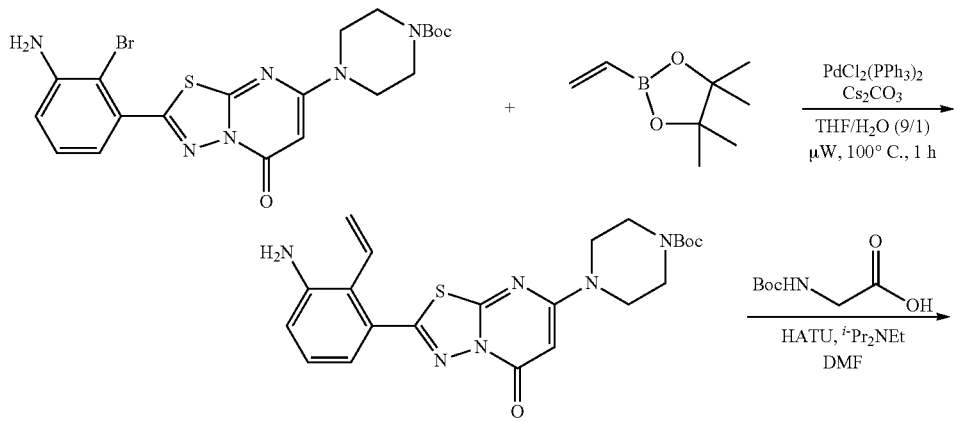

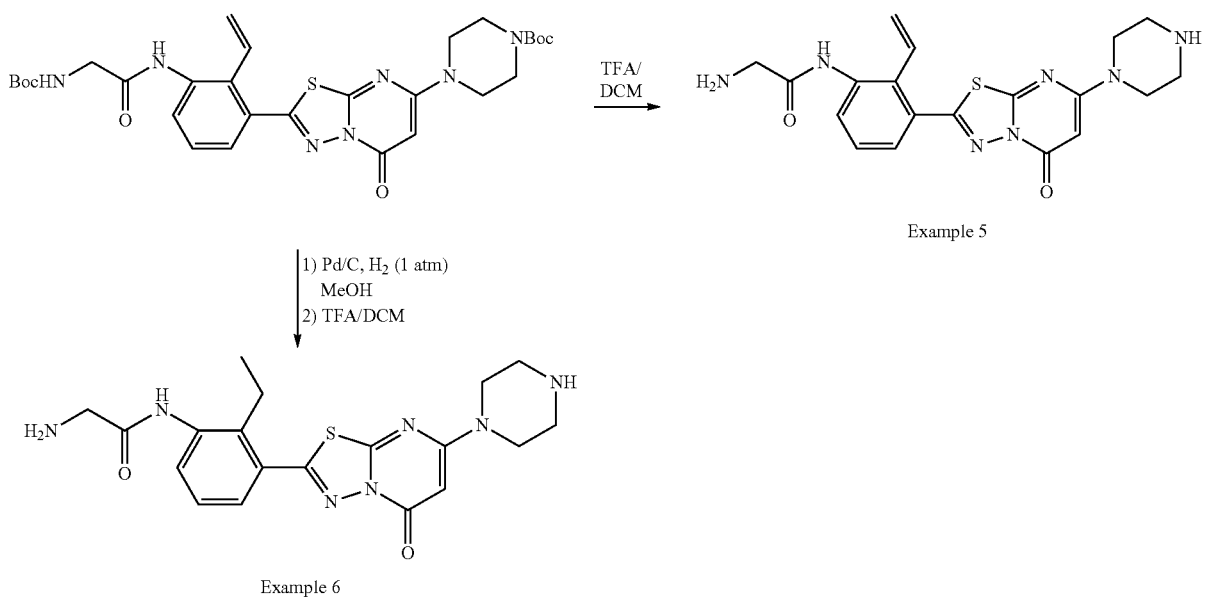

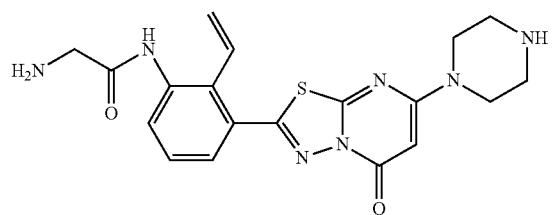 [SMILES: C=Cc1c(NC(=O)CN)cccc1-c1nn2c(=O)cc(N3CCNCC3)nc2s1]

Example 6

Example 5

2-amino-N-(3-(5-oxo-7-(piperazin-1-yl)-5H-[1,3,4]thiadiazolo[3,2-a]pyrimidin-2-yl)-2-vinylphenyl)acetamide For the Suzuki coupling, see WO2009024615, the contents of which are incorporated by reference herein in their entirety. To a solution of tert-butyl 4-(2-(3-amino-2-bromophenyl)-5-oxo-5H-[1,3,4]thiadiazolo[3,2-a]pyrimidin-7-yl)piperazine-1-carboxylate (720 mg, 1.42 mmol) in THF/H$_2$O (12.6 ml/1.4 ml) is added vinylboronic acid pinacol ester (656 mg, 4.26 mmol), PdCl$_2$(PPh$_3$)$_2$ (100 mg, 0.14 mmol) and cesium carbonate (1.39 g, 4.26 mmol) and the mixture is microwaved at 100° C. for 1 h. The mixture is diluted with H$_2$O (30 ml) and extracted with EtOAc (3×30 ml). The combined organic layers are washed with brine and dried over Na$_2$SO$_4$. After removing EtOAc in vacuo, the residue is purified by Biotage column chromatography (MeOH/DCM: 1/100-1/20 gradient) to give desired product (613 mg, 95%) as a light yellow solid.

tert-butyl 4-(2-(3-amino-2-vinylphenyl)-5-oxo-5H-[1,3,4]thiadiazolo-[3,2-a]pyrimidin-7-yl)piperazine-1-carboxylate is carried on as described in steps 5 and 6 of Example 1 to yield 2-amino-N-(3-(5-oxo-7-(piperazin-1-yl)-5H-[1,3,4]thiadiazolo[3,2-a]pyrimidin-2-yl)-2-vinylphenyl)acetamide. $^1$H NMR (400 MHz, DMSO-d$_6$) δ 7.77 (d, J=8.0 Hz, 1H), 7.69 (d, J=8.0 Hz, 1H), 7.55 (t, J=8.0 Hz, 1H), 6.87 (dd, J=18.0, 11.6 Hz, 1H), 6.52 (s, 1H), 5.66 (dd, J=11.6, 1.6 Hz, 1H), 5.62 (s, 1H), 5.45 (d, J=18.0 Hz, 1H), 3.84-3.74 (m, 6H), 3.17 (t, J=4.2 Hz, 4H); LC/MS: $t_R$=2.587 min; HRMS: m/z (M+H$^+$)=412.1545 (Calculated for $C_{19}H_{22}N_7O_2S$=412.1556).

Example 6

2-amino-N-(3-(5-oxo-7-(piperazin-1-yl)-5H-[1,3,4]thiadiazolo[3,2-a]pyrimidin-2-yl)-2-ethylphenyl)acetamide

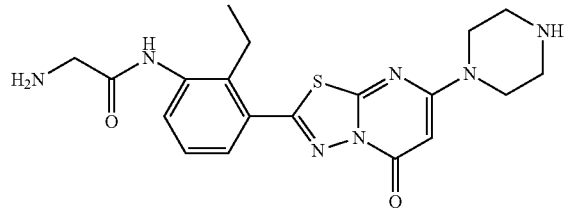 [SMILES: CCc1c(NC(=O)CN)cccc1-c1nn2c(=O)cc(N3CCNCC3)nc2s1]

The compound of this example is prepared using the procedure as similarly described in Example 5 except the vinyl group on tert-butyl 4-(2-(3-(2-((tert-butoxycarbonyl)amino)acetamido)-2-vinylphenyl)-5-oxo-5H-[1,3,4]thiadiazolo[3,2-a]pyrimidin-7-yl)piperazine-1-carboxylate is subjected to hydrogenation by carrying out the reaction under usual condition with Pd/C under 1 atm $H_2$. After removing the catalyst, the crude product is directly used for the next step, deprotection of -Boc groups, without further purification.

$^1$H NMR (400 MHz, DMSO-$d_6$) δ 9.96 (s, 1H), 8.86 (br.s., 1H), 8.10 (br.s., 2H), 7.60 (dd, J=8.0, 1.4 Hz, 1H), 7.51 (dd, J=8.0, 1.4 Hz, 1H), 7.44 (t, J=8.0 Hz, 1H), 5.62 (s, 1H), 3.87 (s, 2H), 3.78 (t, J=5.2 Hz, 4H), 3.16 (t, J=5.2 Hz, 4H), 2.86 (q, J=7.6 Hz, 2H), 1.07 (t, J=7.6 Hz, 3H); LC/MS: $t_R$=2.626 min; HRMS: m/z (M+H$^+$)=414.1708 (Calculated for $C_{19}H_{24}N_7O_2S$=414.1712).

Example 7

2-amino-N-(3-(5-oxo-7-(piperazin-1-yl)-5H-[1,3,4]thiadiazolo[3,2-a]pyrimidin-2-yl)-5-vinylphenyl)acetamide

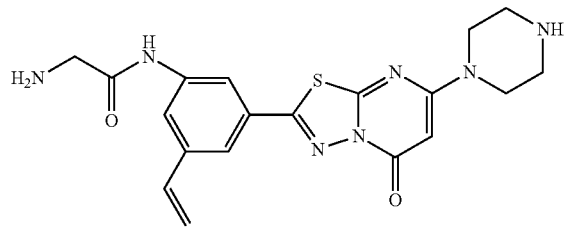 [SMILES: C=Cc1cc(NC(=O)CN)cc(-c2nn3c(=O)cc(N4CCNCC4)nc3s2)c1]

The compound of Example 7 is prepared using similar procedure as described in Example 5 except tert-butyl 4-(2-(3-amino-5-bromophenyl)-5-oxo-5H-[1,3,4]thiadiazolo[3,2-a]pyrimidin-7-yl)piperazine-1-carboxylate is used as the starting material. $^1$H NMR (400 MHz, DMSO-$d_6$) δ 10.83 (s, 1H), 8.20 (t, J=1.6 Hz, 1H), 7.90 (t, J=1.6 Hz, 1H), 7.70 (t, J=1.6 Hz, 1H), 6.87 (dd, J=14.0, 11.2 Hz, 1H), 5.94 (d, J=14.0 Hz, 1H), 5.61 (s, 1H), 5.46 (d, J=11.2 Hz, 1H), 3.84 (s, 2H), 3.79 (t, J=5.2 Hz, 4H), 3.19 (t, J=5.2 Hz, 4H); LC/MS: $t_R$=2.794 min; HRMS: m/z (M+H$^+$)=412.1547 (Calculated for $C_{19}H_{22}N_7O_2S$=412.1556).

Example 8

2-amino-N-(3-(5-oxo-7-(piperazin-1-yl)-5H-[1,3,4]thiadiazolo[3,2-a]pyrimidin-2-yl)-5-ethylphenyl)acetamide

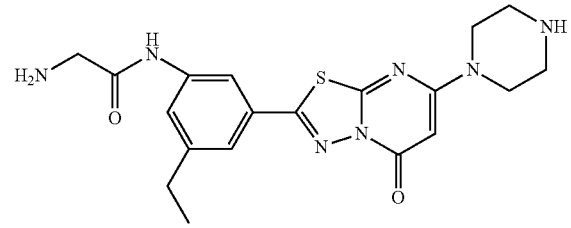 [SMILES: CCc1cc(NC(=O)CN)cc(-c2nn3c(=O)cc(N4CCNCC4)nc3s2)c1]

The compound of Example 8 is prepared using similar procedure as described in Example 6 except tert-butyl 4-(2-(3-amino-5-bromophenyl)-5-oxo-5H-[1,3,4]thiadiazolo[3,2-a]pyrimidin-7-yl)piperazine-1-carboxylate is used as the starting material. $^1$H NMR (400 MHz, DMSO-$d_6$) δ 10.72 (s, 1H), 8.12 (t, J=1.6 Hz, 1H), 7.65 (t, J=1.6 Hz, 1H), 7.49 (t, J=1.6 Hz, 1H), 5.61 (s, 1H), 3.82 (s, 2H), 3.78 (t, J=5.2 Hz, 4H), 3.19 (t, J=5.2 Hz, 4H), 2.72 (q, J=7.6 Hz, 2H), 1.23 (t, J=7.6 Hz, 3H); LC/MS: $t_R$=2.792 min; HRMS: m/z (M+H$^+$)=414.1709 (Calculated for $C_{19}H_{24}N_7O_2S$=414.1712).

Example 9

2-amino-N-(3-methyl-5-(5-oxo-7-(piperazin-1-yl)-5H-[1,3,4]thiadiazolo[3,2-a]pyrimidin-2-yl)phenyl)acetamide

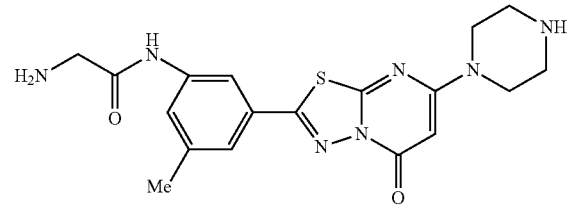

Using the procedures described or similarly described in Example 1, the compound of Example 9 is prepared except 3-methyl-5-nitrobenzoic acid is used as starting material in step 1. $^1$H NMR (400 MHz, DMSO-$d_6$) δ 10.72 (s, 1H), 8.12 (s, 1H), 9.00-8.15 (br.s., 2H), 7.60 (s, 1H), 7.45 (s, 1H), 5.61 (s, 1H), 3.82 (s, 2H), 3.78 (t, J=5.2 Hz, 4H), 3.19 (t, J=5.2 Hz, 4H), 2.67 (s, 1H), 2.41 (s, 3H); LC/MS: $t_R$=2.632 min; HRMS: m/z (M+H$^+$)=(Calculated for $C_{18}H_{22}N_7O_2S$=400.1556).

Example 10

The compound of Example 10 is prepared as described in the procedures below:

Scheme 3:

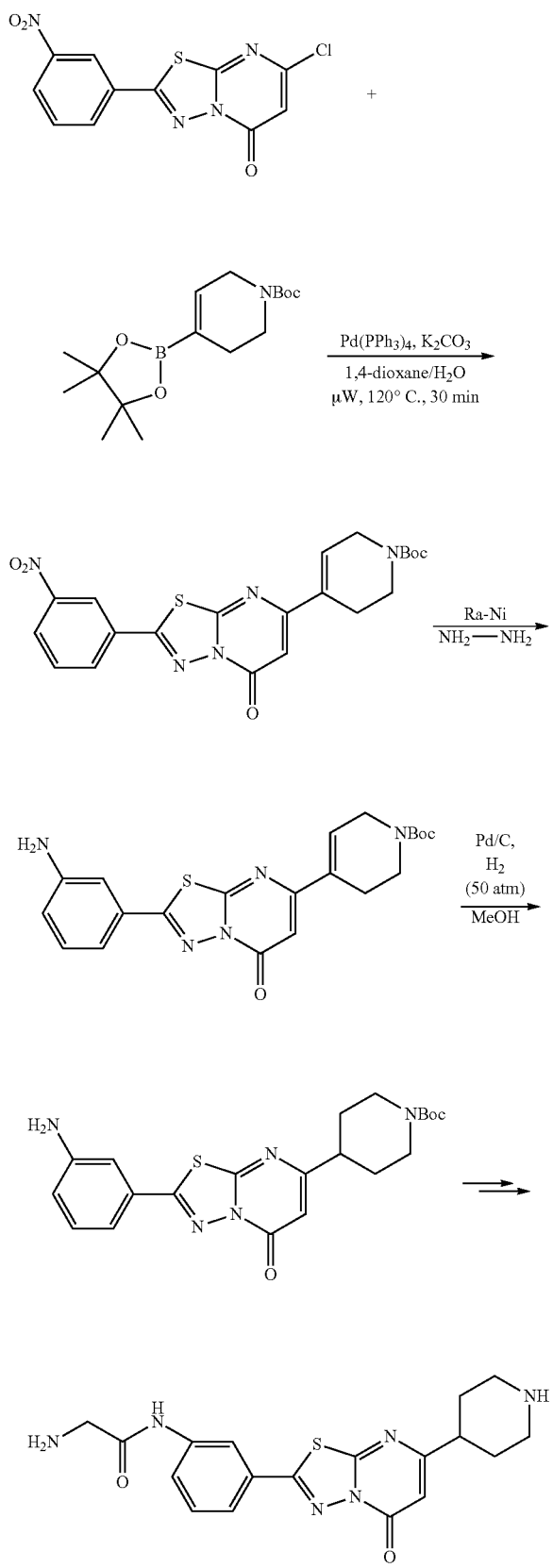

Example 10

2-amino-N-(3-(5-oxo-7-(piperidin-4-yl)-5H-[1,3,4]thiadiazolo[3,2-a]pyrimidin-2-yl)phenyl)acetamide

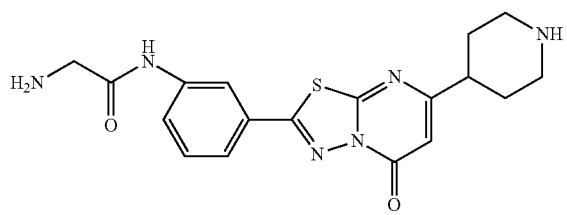

To a solution of 7-chloro-2-(3-nitrophenyl)-5H-[1,3,4]thiadiazolo[3,2-a]pyrimidin-5-one (70 mg, 0.227 mmol) in 1,4-dioxane (2 ml) and water (0.50 ml) is added tert-butyl 4-(4,4,5,5-tetramethyl-1,3,2-dioxaborolan-2-yl)-5,6-dihydropyridine-1(2H)-carboxylate (105 mg, 0.340 mmol), Pd(PPh$_3$)$_4$ (26.2 mg, 0.023 mmol) and K$_2$CO$_3$ (78 mg, 0.567 mmol). The mixture is microwaved at 120° C. for 30 min. After cooling to room temperature, EtOAc (20 ml) and water (10 ml) are added and the organic layer is separated and washed with brine, dried over Na$_2$SO$_4$. After removing EtOAc in vacuo, the crude residue is purified by Biotage column chromatography (MeOH/DCM: 1/100 to 1/20 gradient) to give the desired product (90 mg, 87%) as a light yellow solid. tert-butyl 4-(2-(3-nitrophenyl)-5-oxo-5H-[1,3,4]thiadiazolo[3,2-a]pyrimidin-7-yl)-5,6-dihydropyridine-1(2H)-carboxylate is converted to tert-butyl 4-(2-(3-aminophenyl)-5-oxo-5H-[1,3,4]thiadiazolo[3,2-a]pyrimidin-7-yl)-5,6-dihydropyridine-1(2H)-carboxylate using Raney nickel and hydrazine.

To a solution of tert-butyl 4-(2-(3-aminophenyl)-5-oxo-5H-[1,3,4]thiadiazolo[3,2-a]pyrimidin-7-yl)-5,6-dihydropyridine-1(2H)-carboxylate (50 mg, 0.12 mmol) in MeOH (10 ml) is added Pd/C and the suspension is subjected to hydrogenation under 50 psi H$_2$ atmosphere in a Paar shaker apparatus for 6 h. After the catalyst is filtered through a pad of Celite, the organic solvent is removed and the crude reside is purified by Biotage column chromatography (MeOH/DCM: 1/100 to 1/20) to give the desired product (20 mg, 40%) as a light yellow solid. This light yellow solid is converted to 2-amino-N-(3-(5-oxo-7-(piperidin-4-yl)-5H-[1,3,4]thiadiazolo[3,2-a]pyrimidin-2-yl)phenyl)acetamide using procedures as similarly described in Steps 5 and 6 in Example 1.

$^1$H NMR (400 MHz, DMSO-d$_6$) δ 10.82 (s, 1H), 8.74-8.64 (br.s., 1H), 8.34 (t, J=3.0 Hz, 1H), 8.20-8.13 (br.s., 2H), 7.84 (ddd, J=8.2, 2.2, 1.2 Hz, 1H), 7.70-7.60 (m, 2H), 6.34 (s, 1H), 3.84 (s, 2H), 3.40 (d, J=12.1 Hz, 2H), 3.06-2.94 (m, 2H), 2.92-2.83 (m, 1H), 2.02 (d, J=12.2 Hz, 2H), 1.90-1.78 (m, 2H); LC/MS: t$_R$=2.507 min; HRMS: m/z (M+H$^+$)=(Calculated for C$_{18}$H$_{21}$N$_6$O$_2$S=385.1447).

Examples 11-12

The compounds of Examples 11-12 are prepared as described or similarly described in the procedures below:

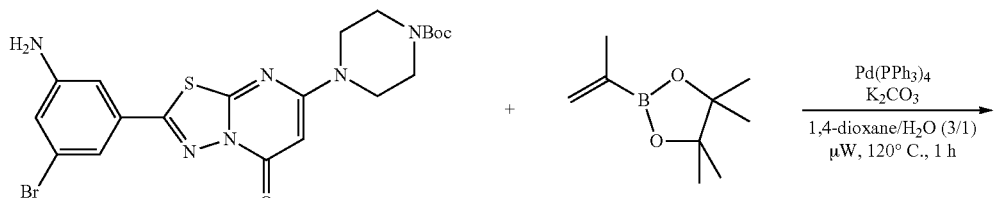

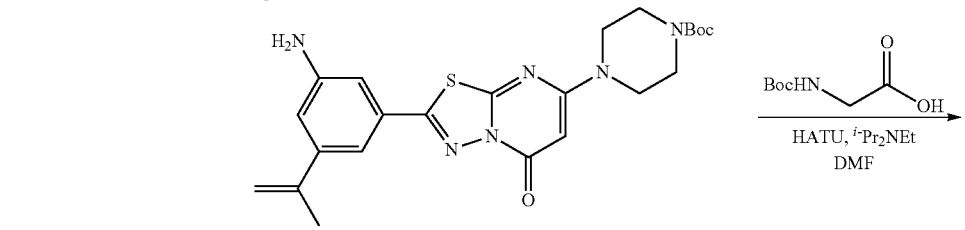

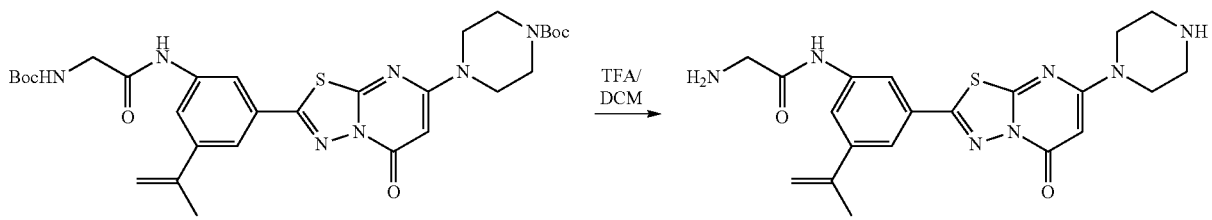

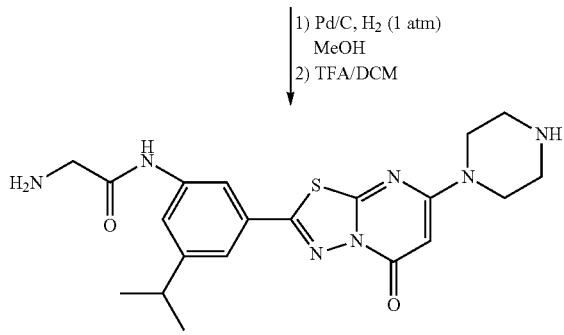

Example 12

Step 1:

To a solution of tert-butyl 4-(2-(3-amino-5-bromophenyl)-5-oxo-5H-[1,3,4]thiadiazolo[3,2-a]pyrimidin-7-yl)piperazine-1-carboxylate, (400 mg, 0.79 mmol), which may be prepared using similar procedures as described in this application, in 1,4-dioxane (7.2 ml) and water (2.4 ml) is added isopropenyl boronic acid pinacol ester (265 mg, 1.577 mmol), Pd(PPh$_3$)$_4$ (91 mg, 0.079 mmol) and potassium carbonate (218 mg, 1.577 mmol). The mixture is microwaved at 120° C. for 1 h. The mixture is diluted with H$_2$O (10 ml), extracted with EtOAc (3×10 ml). The combined organic layers are washed with brine and dried over Na$_2$SO$_4$. After removing EtOAc in vacuo, the residue is purified by Biotage column chromatography (MeOH/DCM: 1/100-1/20 gradient) to give desired product (285 mg, 77%) as a light yellow solid.

Step 2:

To a solution of tert-butyl 4-(2-(3-amino-5-(prop-1-en-2-yl)phenyl)-5-oxo-5H-[1,3,4]thiadiazolo[3,2-a]pyrimidin-7-yl)piperazine-1-carboxylate (375 mg, 0.80 mmol) in DMF (8 ml) is added Boc-Gly-OH (280 mg, 1.60 mmol), HATU (609 mg, 1.60 mmol) and i-Pr$_2$NEt (0.42 ml, 2.40 mmol). The mixture is stirred at room temperature for 2 h. EtOAc (20 ml) is added and the solution is washed with H$_2$O and brine. The organic layer is dried over Na$_2$SO$_4$. After removing EtOAc, the residue is purified by Biotage column chromatography (MeOH/DCM: 1/100 to 1/20 gradient) to give the desired product (416 mg, 83%).

Step 3:

To a solution of tert-butyl 4-(2-(3-(2-((tert-butoxycarbonyl)amino)acetamido)-5-(prop-1-en-2-yl)phenyl)-5-oxo-5H-[1,3,4]thiadiazolo[3,2-a]pyrimidin-7-yl)piperazine-1-carboxylate (50 mg, 0.80 mmol) in DCM (4 ml) is added TFA (1 ml) and the mixture is stirred for 1 h. After the removal of solvent in vacuo, the crude residue is directly purified by preparative HPLC to give the desired product (Example 11).

Step 4:

To a solution of tert-butyl 4-(2-(3-bromo-5-(2-(tert-butoxycarbonylamino)-acetamido)phenyl)-5-oxo-5H-[1,3,4]thiadiazolo[3,2-a]pyrimidin-7-yl)piperazine-1-carboxylate (120 mg, 0.19 mmol) in MeOH (20 ml) is added Pd/C (100 mg, 10 wt % Pd). The hydrogenation is carried out under 1 atm hydrogen atmosphere overnight. After removing the catalyst and solvent, the crude product is directly used for the next step deprotection of -Boc (1/4 of TFA/DCM, v/v) and preparative HPLC purification to give the desired product (Example 12).

Example 11

2-amino-N-(3-(5-oxo-7-(piperazin-1-yl)-5H-[1,3,4]thiadiazolo[3,2-a]pyrimidin-2-yl)-5-(prop-1-en-2-yl)phenyl)acetamide

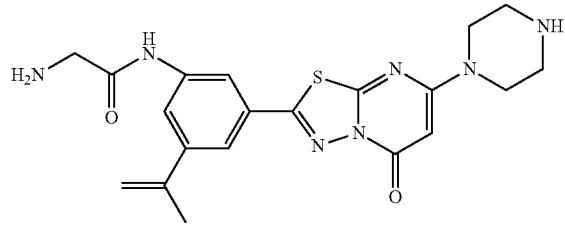 [SMILES: C=C(C)c1cc(NC(=O)CN)cc(-c2nn3c(=O)cc(N4CCNCC4)nc3s2)c1]

$^1$H NMR (400 MHz, DMSO-$d_6$) δ 10.86 (s, 1H), 9.00-8.63 (br.s., 1H), 8.27 (t, J=1.8 Hz, 1H), 8.25-8.15 (br.s., 2H), 7.96 (t, J=1.8 Hz, 1H), 7.71 (t, J=1.8 Hz, 1H), 5.67 (s, 1H), 5.59 (s, 1H), 5.35 (t, J=1.0 Hz, 1H), 3.89 (s, 2H), 3.84 (t, J=5.2 Hz, 4H), 3.24 (t, J=5.2 Hz, 4H), 2.22 (s, 3H); LC/MS: $t_R$=2.905 min; HRMS: m/z (M+H$^+$)=(Calculated for $C_{20}H_{24}N_7O_2S$=426.1712).

Example 12

2-amino-N-(3-isopropyl-5-(5-oxo-7-(piperazin-1-yl)-5H-[1,3,4]thiadiazolo[3,2-a]pyrimidin-2-yl)phenyl)acetamide

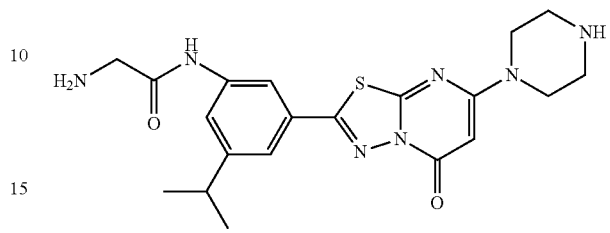

$^1$H NMR (400 MHz, DMSO-$d_6$) δ 10.72 (s, 1H), 8.95-8.80 (br.s., 1H), 8.25-8.15 (br.s., 2H), 8.11 (t, J=1.8 Hz, 1H), 7.68 (t, J=1.8 Hz, 1H), 7.50 (t, J=1.8 Hz, 1H), 5.61 (s, 1H), 3.82 (s, 2H), 3.78 (t, J=5.2 Hz, 4H), 3.19 (t, J=5.2 Hz, 4H), 3.08-2.98 (m, 1H), 1.26 (s, 3H), 1.25 (s, 3H); LC/MS: $t_R$=2.886 min; HRMS: m/z (M+H$^+$)=(Calculated for $C_{20}H_{26}N_7O_2S$=428.1869).

Examples 13-14

The compounds of Examples 13-14 are prepared as described or similarly described in the procedures below:

Scheme 4:

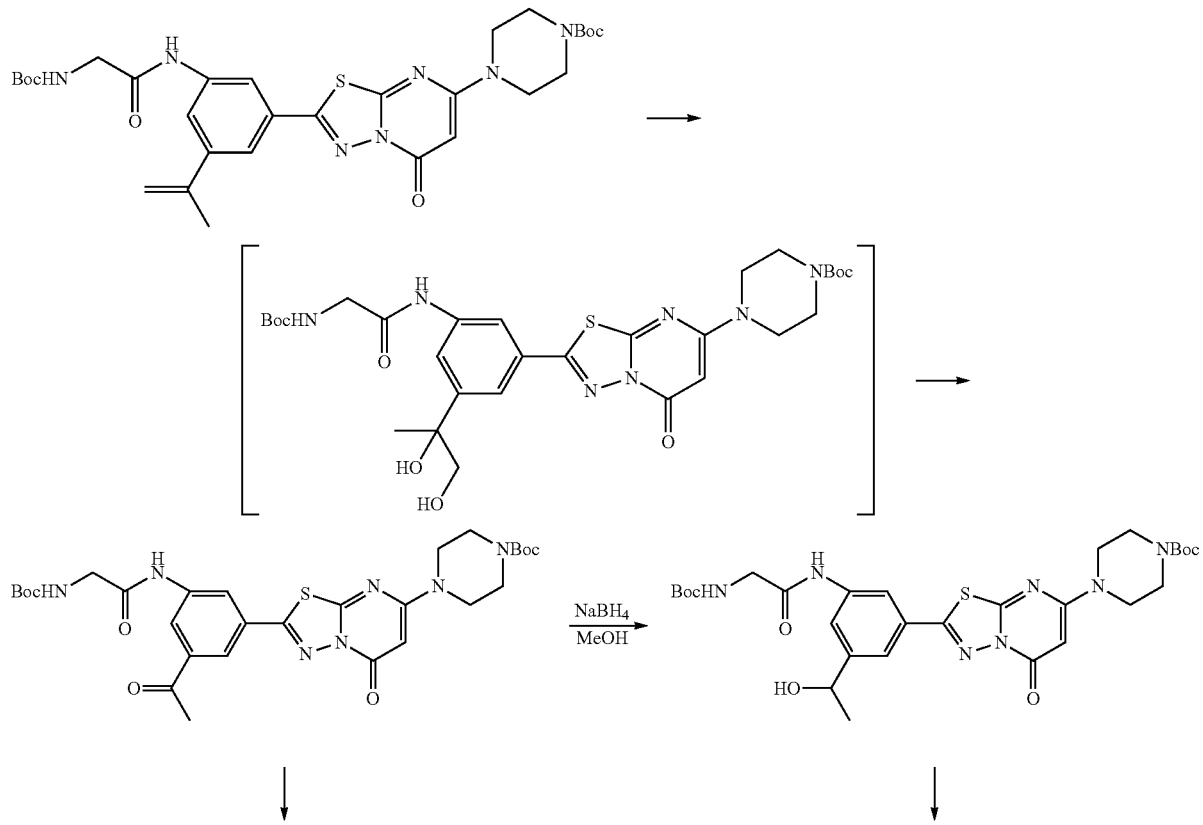

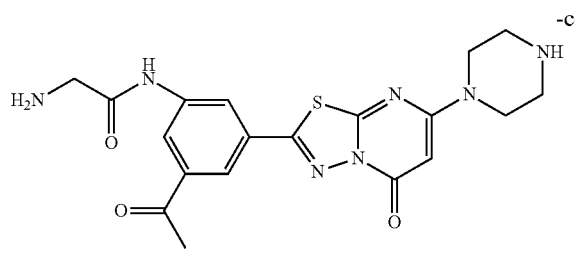

Example 13

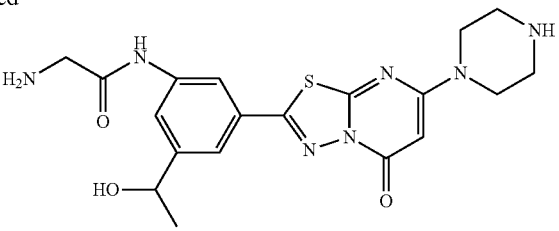

Example 14

Example 13

N-(3-acetyl-5-(5-oxo-7-(piperazin-1-yl)-5H-[1,3,4]thiadiazolo[3,2-a]pyrimidin-2-yl)phenyl)-2-aminoacetamide For the oxidation of alkene to ketone, see *Angew. Chem. Int. Ed.*, 2011, 50, 3497-3450, the contents of which are incorporated by reference in their entirety. To a solution of tert-butyl 4-(2-(3-(2-(tert-butoxycarbonylamino)acetamido)-5-(prop-1-en-2-yl)phenyl)-5-oxo-5H-[1,3,4]thiadiazolo[3,2-a]pyrimidin-7-yl)piperazine-1-carboxylate (103 mg, 0.165 mmol) in THF (1 ml)/acetone (1.000 mL)/water (0.2 ml) cooled with ice/water is added NMO (97 mg, 0.825 mmol). Then OsO$_4$ in t-BuOH solution (0.100 ml, 2.5 wt %, 7.97 μmol) is added and the mixture is stirred at room temperature for 5 h. LC/MS shows the total disappearance of starting material. Then 10% Na$_2$S$_2$O$_4$ aqueous solution (2 ml) is added and the mixture is stirred for 1 h. and extracted with EtOAc (2×10 ml). The combined organic layers are dried over Na$_2$SO$_4$. Biotage column chromatography (MeOH/DCM: 1/100 to 1/10 gradient) gives the desired dihydroxylate (27 mg, 25%) as a white solid.

To a solution of tert-butyl 4-(2-(3-(2-(tert-butoxycarbonylamino)-acetamido)-5-(1,2-dihydroxypropan-2-yl)phenyl)-5-oxo-5H-[1,3,4]thiadiazolo[3,2-a]pyrimidin-7-yl)piperazine-1-carboxylate (27.0 mg, 0.041 mmol) in THF (0.5 ml)/Water (0.500 ml) is added NaIO$_4$ (17.5 mg, 0.082 mmol). The mixture is stirred at room temperature for 2 h and then extracted with EtOAc (2×10 ml). The combined organic layers are washed with brine and dried over Na$_2$SO$_4$. After the removal of organic solvent in vacuo, the crude product (26 mg) is directly used without further purification for the next step as described in Step 6 of Example 1.

$^1$H NMR (400 MHz, DMSO-d$_6$) δ 12.75-12.50 (br.s., 1H), 9.45 (s, 1H), 7.77 and 7.75 (s, 1H), 7.32 and 7.30 (d, J=5.0 Hz, 1H), 6.02 (s, 1H), 5.00 (t, J=7.0 Hz, 1H), 4.35-4.27 (m, 1H), 3.85-3.70 (m, 2H), 3.65 (s, 3H), 3.40-3.25 (m, 2H), 3.24-2.90 (m, 4H); LC/MS: t$_R$=2.576 min; HRMS: m/z (M+H$^+$)=(Calculated for C$_{19}$H$_{22}$N$_7$O$_3$5=428.1505).

Example 14

2-amino-N-(3-(1-hydroxyethyl)-5-(5-oxo-7-(piperazin-1-yl)-5H-[1,3,4]thiadiazolo[3,2-a]pyrimidin-2-yl)phenyl)acetamide The compound of this example is prepared as described in Example 13 above except that the acetyl group of tert-butyl 4-(2-(3-acetyl-5-(2-((tert-butoxycarbonyl)amino)-acetamido)phenyl)-5-oxo-5H-[1,3,4]thiadiazolo[3,2-a]pyrimidin-7-yl)piperazine-1-carboxylate is further reduced to tert-butyl 4-(2-(3-(2-((tert-butoxycarbonyl)amino)acetamido)-5-(1-hydroxyethyl)phenyl)-5-oxo-5H-[1,3,4]thiadiazolo[3,2-a]pyrimidin-7-yl)piperazine-1-carboxylate using sodium borohydride. The resulting product is then deprotected as described in Step 6 of Example 1. $^1$H NMR (400 MHz, DMSO-d$_6$) δ 10.73 (s, 1H), 8.95-8.80 (br.s., 2H), 8.16 (t, J=1.8 Hz, 1H), 8.16-8.07 (br.s., 2H), 7.76 (t, J=1.8 Hz, 1H), 7.59 (s, J=1.8 Hz, 1H), 5.61 (s, 1H), 5.50-5.45 (br.s., 1H), 4.83 (q, J=6.7 Hz, 1H), 3.81 (s, 2H), 3.78 (t, J=5.2 Hz, 4H), 3.19 (t, J=5.2 Hz, 4H), 1.36 (d, J=6.7 Hz, 3H); LC/MS: t$_R$=2.417 min; HRMS: m/z (M+H$^+$)=(Calculated for C$_{19}$H$_{24}$N$_7$O$_3$S=430.1661).

Example 14-A
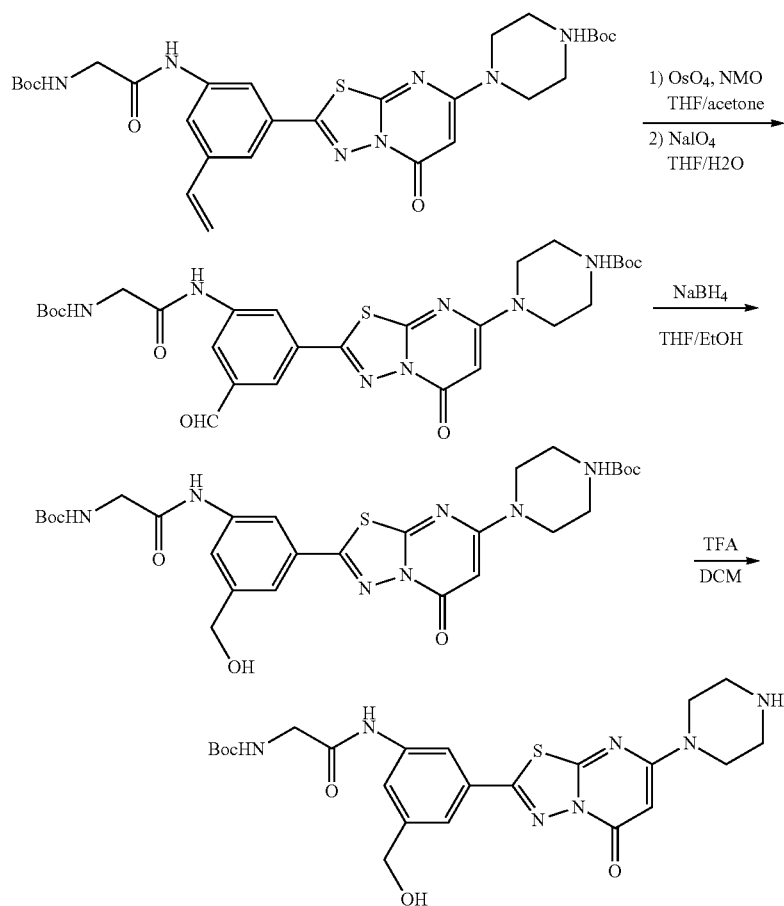
The compound of this example may be prepared according to the procedure described or similarly described in Example 14.
Examples 14-B and 14-C
The compounds of Examples 14-B and 14-C are prepared as described or similarly described in the procedures below:
Example 14-B
2-amino-N-(4-(5-oxo-7-(piperazin-1-yl)-5H-[1,3,4]thiadiazolo[3,2-a]pyrimidin-2-yl)pyridin-2-yl)acetamide
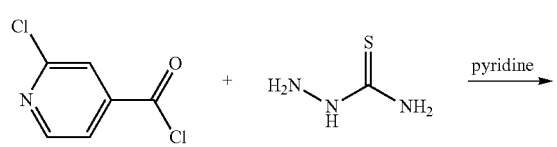
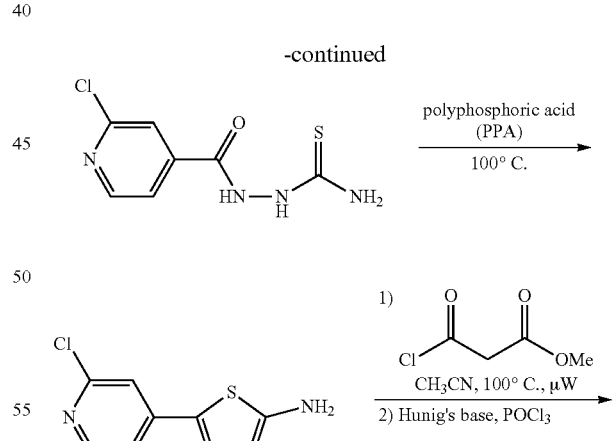
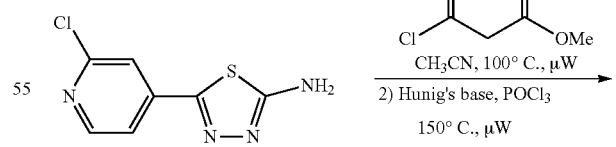
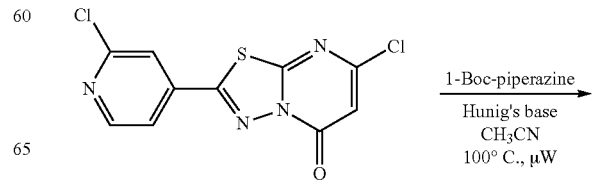

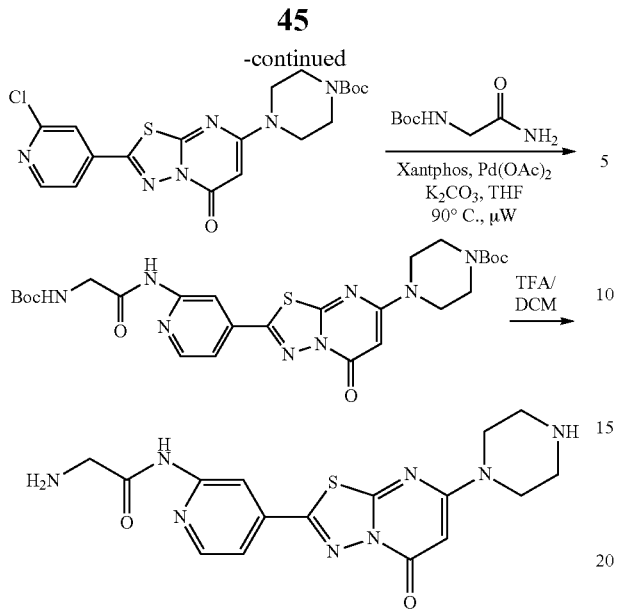

Step 1:

To a suspension of thiosemicarbazide (0.52 g, 5.68 mmol) in pyridine (3 ml) cooled with ice/water is added 2-chloroisonicotinoyl chloride (1.00 g, 5.68 mmol) dropwise. The addition is completed in 20 min. Then the mixture is allowed to warm to room temperature and stirred for 4 h. The mixture is poured into ice/water and the solid starts to precipitate. The solid is filtered and washed with minimum amount of EtOAc to remove impurities to give the desired product as a white solid (0.60 g, 46%).

Step 2:

Polyphosphoric acid (PPA) (20 ml) is preheated at 100° C. To this hot PPA is added 2-(2-chloroisonicotinoyl)hydrazinecarbothioamide (3.50 g, 15.17 mmol) portionwise. After the addition, the mixture is further stirred at this temperature for 1 h. After cooling to room temperature, the mixture is slowly poured into ice and the pH is adjusted to 9.0 with addition of ammonium hydroxide solution (37 wt % in water). The solid precipitates out and is filtered, washed with EtOAc (3×50 ml). The EtOAc is combined and washed with brine, dried over sodium sulfate. After the removal of most EtOAc, the solid is filtered which is combined with the solid obtained in the first filtration to give a light yellow solid (2.80 g, 87%).

Step 3:

To a solution 5-(2-chloropyridin-4-yl)-1,3,4-thiadiazol-2-amine (0.500 g, 2.35 mmol) in CH$_3$CN (13 ml) is added methyl 3-chloro-3-oxopropanoate (0.278 ml, 2.59 mmol). The mixture is microwaved at 100° C. for 12 min. After cooling to room temperature, POCl$_3$ (4.37 ml, 47 mmol) and Hunig's base (0.411 ml, 2.35 mmol) is added and the mixture is microwaved at 150° C. for 30 min. After cooling to room temperature, excess POCl$_3$ and CH$_3$CN are removed in vacuo and the residue is dissolved in DCM and poured into ice. The DCM solution is washed with saturated aqueous NaHCO$_3$ solution and the organic layer is separated (due to the formation of polyphosphoric acid, filtration of the organic and aqueous layers through Celite is needed to remove the sticky material). The organic layer is washed with brine, dried over Na$_2$SO$_4$. After the removal of organic solvent in vacuo, the crude residue is purified by Biotage column chromatography (EtOAc/DCM: 1/100 to 1/20 gradient) to give the desired product (120 mg, 17%) as a yellow solid.

Step 4:

To a mixture of 7-chloro-2-(2-chloropyridin-4-yl)-5H-[1,3,4]thiadiazolo[3,2-a]pyrimidin-5-one (300 mg, 1.17 mmol) and tert-butyl piperazine-1-carboxylate (240 mg, 1.29 mmol) in CH$_3$CN (12 ml) is added Hunig's base (0.245 ml, 1.40 mmol) and the mixture is microwaved at 100° C. for 2 h. After cooling to room temperature, solid starts to precipitate out. The solid is filtered and washed with EtOAc and collected. The filtrate is concentrated in vacuo and the crude residue is purified by Biotage column chromatography (MeOH/DCM: 1/100 to 1/10 gradient) to give another portion of product. The total amount of desired product is 446 mg (yield: 82%).

Step 5:

To a solution of tert-butyl 4-(2-(2-chloropyridin-4-yl)-5-oxo-5H-[1,3,4]thiadiazolo[3,2-a]pyrimidin-7-yl)piperazine-1-carboxylate (160 mg, 0.36 mmol) in THF (5 ml) are added Boc-gly-NH$_2$ (124 mg, 0.72 mmol), XantPhos (124 mg, 0.14 mmol), Pd(OAc)$_2$ (24 mg, 0.07 mmol) and K$_2$CO$_3$ (197 mg, 1.44 mmol). The microwave tube is purged with nitrogen for 1 min then sealed. The mixture is microwaved at 90° C. for 2 h. After cooling to room temperature, EtOAc (30 ml) and water (30 ml) are added. The organic layer is separated, washed with brine and dried over sodium sulfate. After the removal of organic solvent in vacuo, the residue is purified through Biotage column chromatography (MeOH/DCM=1/100 to 5/20) to give the desired product (188 mg, 90%).

Step 6:

To a solution of tert-butyl 4-(2-(2-(2-((tert-butoxycarbonyl)amino)acetamido)pyridin-4-yl)-5-oxo-5H-[1,3,4]thiadiazolo[3,2-a]pyrimidin-7-yl)piperazine-1-carboxylate (50 mg, 0.085 mmol) in DCM (1 ml) is added TFA (0.25 ml) and the mixture is stirred at room temperature for 2 h. The solvent is removed in vacuo and the residue is directly purified through preparative HPLC to give the desired 2-Amino-N-(4-(5-oxo-7-(piperazin-1-yl)-5H-[1,3,4]thiadiazolo[3,2-a]pyrimidin-2-yl)pyridin-2-yl)acetamide. $^1$H NMR (400 MHz, DMSO-d$_6$) δ 11.31 (s, 1H), 9.10-8.60 (br.s., 2H), 8.61 (d, J=5.1 Hz, 1H), 8.58 (s, 1H), 8.35-8.05 (br.s., 3H), 7.66 (dd, J=5.1, 1.6 Hz, 1H), 5.63 (s, 1H), 3.92 (s, 2H), 3.79 (t, J=4.7 Hz, 4H), 3.19 (t, J=4.7 Hz, 4H); LC/MS: t$_R$=2.163 min; HRMS: m/z (M+H$^+$)=387.1346 (Calculated for C$_{16}$H$_{19}$N$_8$O$_2$S=387.1352).

Example 14-C

2-Amino-N-(5-(5-oxo-7-(piperazin-1-yl)-5H-[1,3,4]thiadiazolo[3,2-a]pyrimidin-2-yl)pyridin-3-yl)acetamide

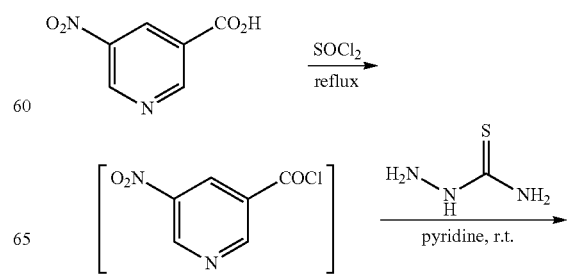

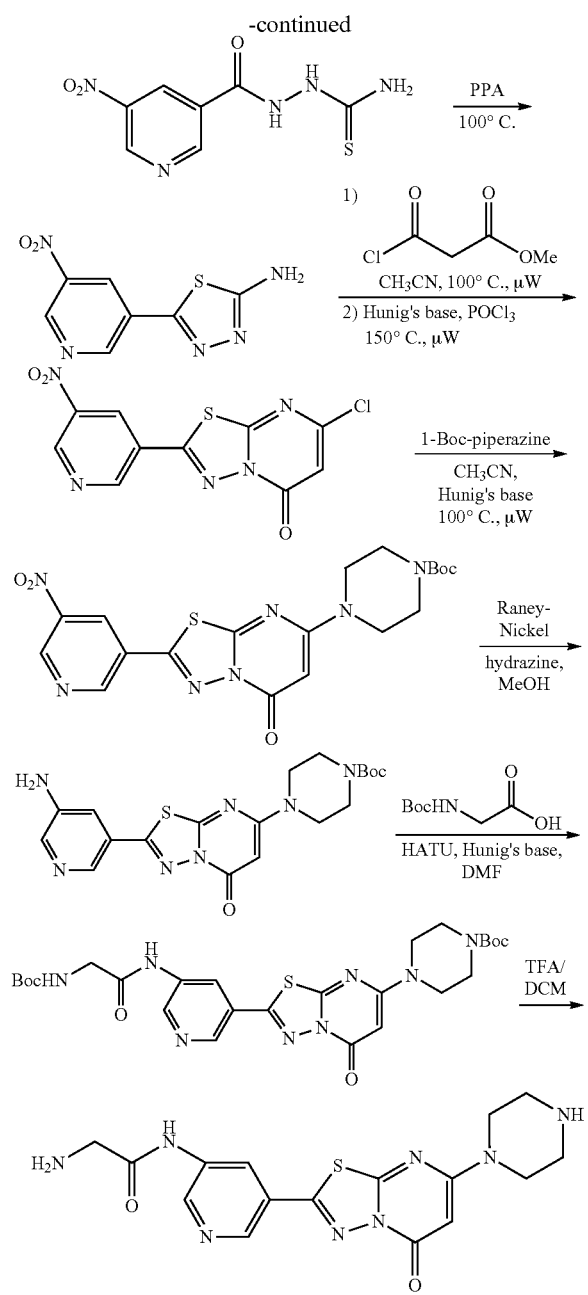

Step 1:
5-nitronicotinic acid (500 mg, 2.97 mmol) is mixed with thionyl chloride (15 ml, 206 mmol) and the mixture is heated at 80° C. for 3.5 h. After the removal of thionyl chloride, the residue is dissolved in pyridine (2 ml) and thiosemicarbazide (271 mg, 2.97 mmol) is added. The mixture is stirred overnight at room temperature. The mixture is poured into ice and the precipitate is filtered and washed with EtOAc to give the desired product as a gray solid (110 mg, 15%).

Step 2:
PPA (2 ml) is preheated to 100° C. and the 2-(5-nitronicotinoyl)hydrazinecarbothioamide (110 mg, 0.46 mmol) is added portionwise. The mixture is heated at this temperature for 1 h. After cooling to room temperature, the mixture is slowly poured into ice and the pH is adjusted to 9.0 with the addition of ammonium hydroxide solution (37 wt % in water). The solid precipitates out and is filtered and washed with EtOAc (3×5 ml). The EtOAc is combined, washed with brine and dried over sodium sulfate. After the removal of most EtOAc, the solid is filtered which is combined with the solid obtained in the first filtration to give a light yellow solid (100 mg, 98%).

Step 3:
Step 3: To a solution 5-(5-nitropyridin-3-yl)-1,3,4-thiadiazol-2-amine (80 mg g, 0.36 mmol) in $CH_3CN$ (3.4 ml) is added methyl 3-chloro-3-oxopropanoate (0.054 ml, 0.50 mmol). The mixture is microwaved at 100° C. for 12 min. After cooling to room temperature, $POCl_3$ (1.34 ml, 14.34 mmol) and Hunig's base (0.063 ml, 0.36 mmol) are added and the mixture is microwaved at 150° C. for 30 min. After cooling to room temperature, excess $POCl_3$ and $CH_3CN$ are removed in vacuo and the residue is dissolved in DCM and poured into ice. The DCM solution is washed with saturated aqueous $NaHCO_3$ solution and the organic layer is separated (due to the formation of polyphosphoric acid, filtration of the organic and aqueous layers through Celite is needed to remove the sticky material). The organic layer is washed with brine and dried over $Na_2SO_4$. After the removal of organic solvent in vacuo, the crude residue is purified by Biotage column chromatography (EtOAc/DCM: 1/100 to 1/20 gradient) to give the desired product (30 mg, 27%) as a yellow solid.

Step 4:
To a mixture of 7-chloro-2-(2-chloropyridin-4-yl)-5H-[1,3,4]thiadiazolo[3,2-a]pyrimidin-5-one (30 mg, 0.097 mmol) and tert-butyl piperazine-1-carboxylate (22 mg, 0.12 mmol) in $CH_3CN$ (2 ml) is added Hunig's (0.024 ml, 0.140 mmol) and the mixture is microwaved at 100° C. for 1 h. After cooling to room temperature, solid starts to precipitate out. The solid is filtered, washed with EtOAc and collected. The filtrate is concentrated in vacuo and the crude residue is purified by Biotage column chromatography (MeOH/DCM: 1/100 to 1/10 gradient) to give another portion of product. The total amount of desired product is 40 mg (yield: 90%).

Step 5:
To a solution of tert-butyl 4-(2-(5-nitropyridin-3-yl)-5-oxo-5H-[1,3,4]thiadiazolo[3,2-a]pyrimidin-7-yl)piperazine-1-carboxylate (40 mg, 0.087 mmol) in MeOH (3 ml) is added Raney-nickel in water slurry. Then hydrazine (0.027 ml, 0.87 mmol) is added dropwise. After the completion of addition, the mixture is stirred for another 5 min, then filtered through a pad of Celite to remove the catalyst. The filtrate is concentrated in vacuo and dried under vacuo to give the desired product (20 mg, 54%).

Step 6:
To a solution of tert-butyl 4-(2-(5-aminopyridin-3-yl)-5-oxo-5H-[1,3,4]thiadiazolo[3,2-a]pyrimidin-7-yl)piperazine-1-carboxylate (20 mg, 0.047 mmol) in DMF (1 ml) is added Boc-gly-OH (16 mg, 0.093 mmol), HATU (35 mg, 0.093 mmol) and Hunig's base (0.024 mmol, 0.14 mmol) and the mixture is stirred at room temperature for 3 h. EtOAc (10 ml) is added and the solution is washed with $H_2O$ and brine. The organic layer is dried over $Na_2SO_4$. After removing EtOAc in vacuo, the residue is purified by Biotage column chromatography (MeOH/DCM: 1/100 to 1/10 gradient) to give the desired product (20 mg, 73%).

Step 7:
To a solution of tert-butyl 4-(2-(5-(2-(tert-butoxycarbonylamino)acetamido)pyridin-3-yl)-5-oxo-5H-[1,3,4]thiadiazolo[3,2-a]pyrimidin-7-yl)piperazine-1-carboxylate (20 mg, 0.034 mmol) in DCM (2 ml) is added TFA (0.5 ml). The mixture is stirred for 2 h, concentrated in vacuo and the residue is directly purified by preparative HPLC to give the desired product 2-Amino-N-(5-(5-oxo-7-(piperazin-1-yl)-

5H-[1,3,4]thiadiazolo[3,2-a]pyrimidin-2-yl)pyridin-3-yl)acetamide: $^1$H NMR (400 MHz, DMSO-$d_6$) δ 11.11 (s, 1H), 9.10-8.90 (br.s., 2H), 8.94 (d, J=2.0 Hz, 1H), 8.83 (d, J=2.0 Hz, 1H), 8.67 (t, J=2.0 Hz, 1H), 8.35-8.15 (br.s., 3H), 5.62 (s, 1H), 3.89 (s, 2H), 3.85 (t, J=5.2 Hz, 4H), 3.20 (t, J=5.2 Hz, 4H); LC/MS: $t_R$=1.908 min; HRMS: m/z (M+H$^+$)=387.1344 (Calculated for $C_{16}H_{19}N_8O_2S$=387.1352).

Example 14-D

The compound of Formula P, wherein A is nitrogen, B is carbon, $R_2$ is fluoro and $R_3$ and $R_4$ are hydrogen may be prepared as described or similarly described below:

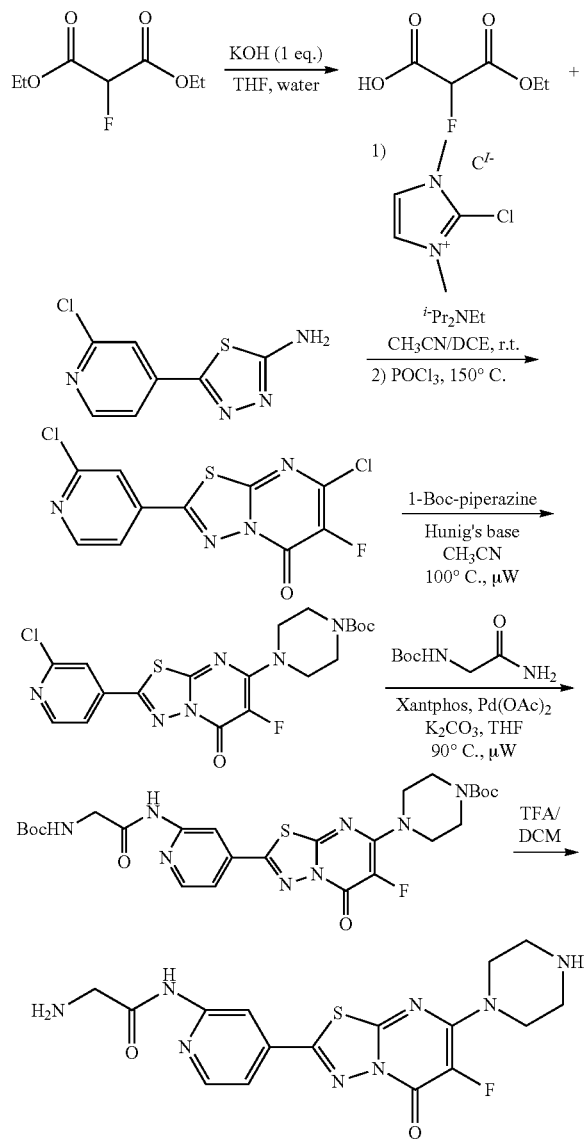

Note: DCE = 1,2-dichloroethane

Example 14-E

The compound of Formula P-II, wherein A is nitrogen, $R_2$ is hydrogen may be prepared using a procedure described or similarly described below:

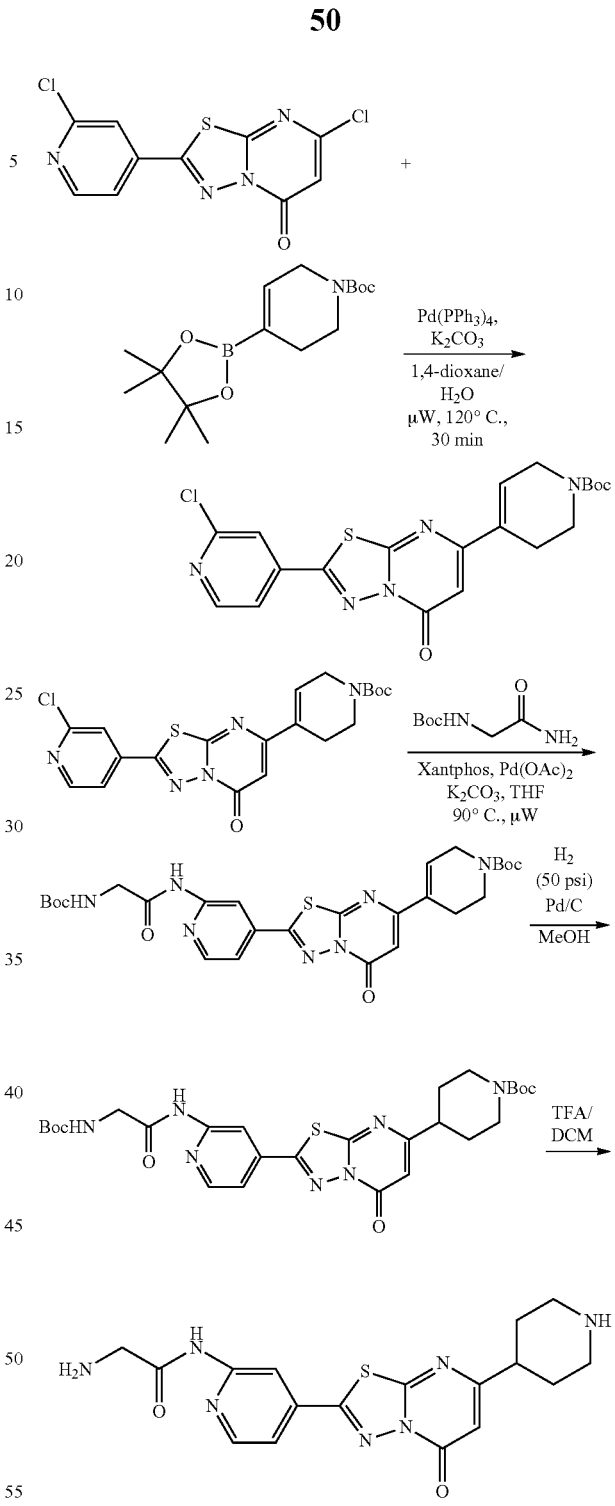

The starting material may be prepared by using the procedures described or similarly described above in Example 14-D.

Example 14-F

The compound of Formula P-II, wherein A is nitrogen, $R_2$ is fluoro may be prepared using a procedure described or similarly described below:

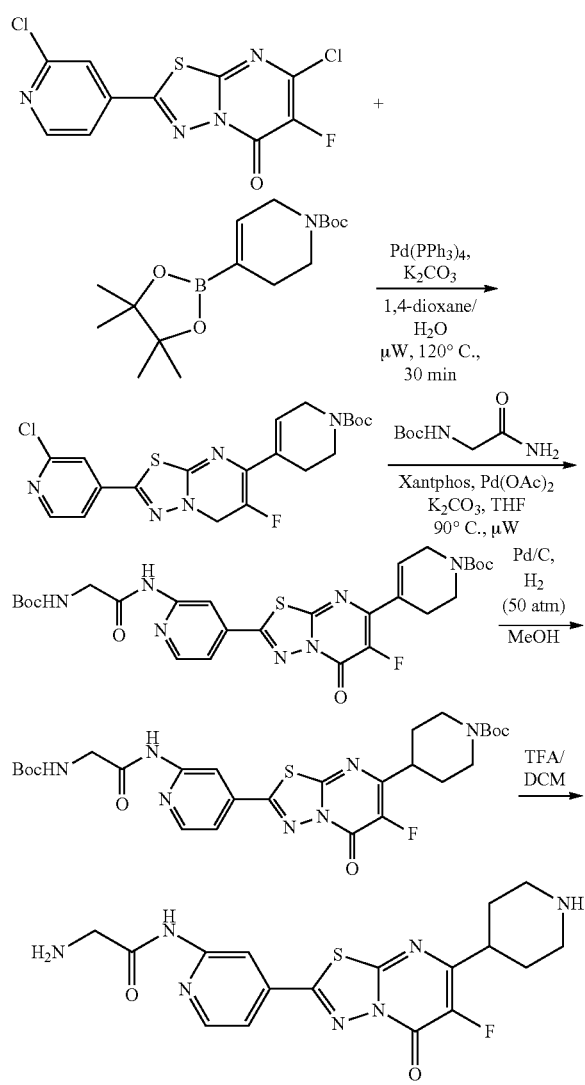

The starting material may be prepared by using the procedures described or similarly described above.

Example 15

Platelet Adhesion and/or Aggregation

To determine platelet adhesion and/or aggregation, the platelet adhesion assay may be conducted by a modification of the assay as described in Blue et al., *Blood* 2008, 111, 1248, the contents of which are incorporated by reference in their entirety. Thirty microliters of human fibrinogen (50 µg/mL) in Tris/saline (100 mM NaCl, 50 mM Tris/HCl, pH 7.4; American Diagnostica, Stamford, Conn.) may be added to black, clear-bottom, untreated polystyrene, nonsterile 384-well microtiter plate wells (Corning no. 3711; Acton, Mass.). After incubating at 22° C. for 1 hour, plates may be washed 3 times with Tris/saline, and wells are ma be blocked with HBMT (138 mM NaCl, 12 mM NaHCO$_3$, 10 mM HEPES, 2.7 mM KCl, 0.4 mM NaH$_2$PO$_4$, 0.1% glucose, 0.35% BSA, pH 7.4) for at least 1 hour. An additional wash may be performed using HBMT with 1 mM MgCl$_2$ and 2 mM CaCl$_2$. Calcein-labeled platelets (final concentration $1 \times 10^{11}$/L) may be treated with Compounds of the Invention (final concentration of 100 µM, 30 µM, 10 µM or 1 µM) at 22° C. for 20 minutes. Thirty microliters of platelets may then be added to the wells. After 1 hour of adhesion, wells may be washed 3 times with HBMT-1 mM MgCl$_2$/2 mM CaCl$_2$ and the plates may be read by a fluorescent microtiter plate reader (Envision; Perkin Elmer) to detect calcein fluorescence (490 nm excitation and 515 nm emission). Negative controls consist of wells containing platelets without compounds of the invention. Positive controls are wells containing platelets and known inhibitors of αIIbβ3, including mAbs 7E3 and 10E5, and EDTA.

The platelet aggregation assay may be conducted by modification of the assay as disclosed in Blue et al., *Blood* 2008, 111, 1248, the contents of which are incorporated by reference in their entirety. Citrated platelet-rich plasma (PRP), may be generated by the centrifugation of whole blood at 650 g for 4 minutes at 22° C., and may then be incubated in aggregometer cuvettes with Compounds of the Invention (final concentration of 100 µM, 30 µM, 10 µM, 1 µM, 0.30 µM, 0.1 µM, 0.03 µM and 0.01 µM) or controls for 15 minutes at 37° C. After 30 seconds in the aggregometer (Bio/Data PAP8; Horsham, Pa.) at 37° C. with stirring, ADP (5-20 µM) may be added to induce aggregation and the light transmittance is measured for 8 minutes. The initial slopes of aggregation in the presence of different concentrations of the Compound tested may be used to generate an IC$_{50}$.

It is expected that the platelet adhesion and/or aggregation studies of various Compounds of the Invention will exhibit an IC$_{50}$ value of less than 100 µM in a platelet aggregation study and/or inhibition of greater than 20%, preferably, greater than 30% at a concentration of 100 µM in a platelet adhesion study.

Using the platelet aggregation assay as similarly described above, the compound of Examples 14-B and 14-C inhibit platelet aggregation with an IC$_{50}$ of 53.6±15.5 nM and 62.0±10.0 nM, respectively.

What is claimed is:

1. A compound of Formula P:

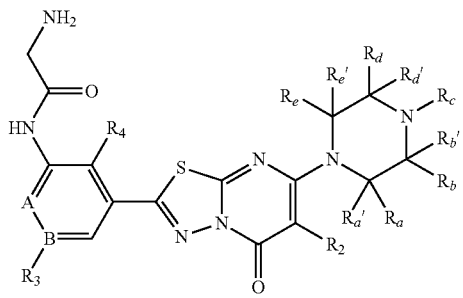

Formula P wherein:
i) A is nitrogen and B is carbon; or B is nitrogen and A is carbon and $R_3$ is absent;
ii) $R_2$ is H or halo;
iii) $R_a$, $R_a'$, $R_b$, $R_b'$, $R_c$, $R_d$, $R_d'$, $R_e$, and $R_e'$ are H;
iv) $R_3$, when present, and $R_4$ are independently hydrogen, halo, $C_{1-4}$alkyl, halo$C_{1-4}$alkyl, hydroxy-$C_{1-4}$alkyl, or acetyl;

in free or salt form.

2. A compound of Formula I:

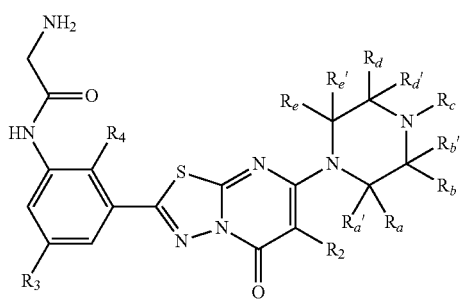

Formula I wherein:
i) $R_2$ is H;
ii) $R_a$, $R_a'$, $R_b$, $R_b'$, $R_c$, $R_d$, $R_d'$, $R_e$, and $R_e'$ are H;
iii) $R_3$ and $R_4$ are independently hydrogen, halo, $C_{1-4}$alkyl, halo$C_{1-4}$alkyl, hydroxy-$C_{1-4}$alkyl or acetyl, provided $R_3$ and $R_4$ are not both hydrogen;

in free or salt form.

3. The compound according to claim 1, selected from the group consisting of:

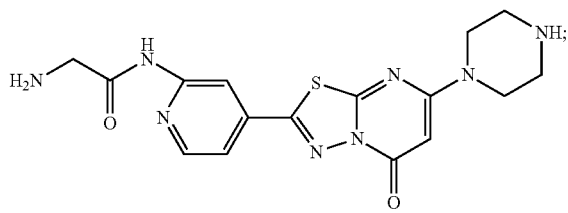

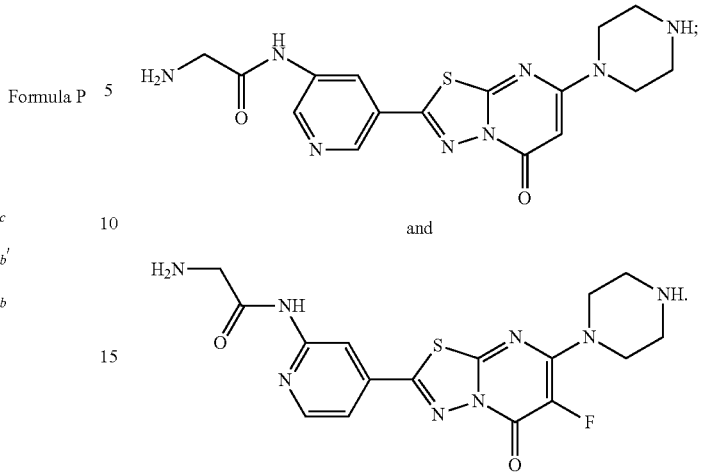

and

4. The compound according to claim 2, selected from the group consisting of:

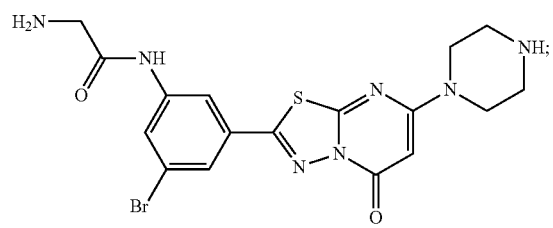

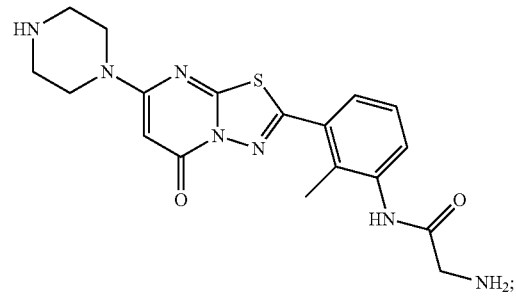

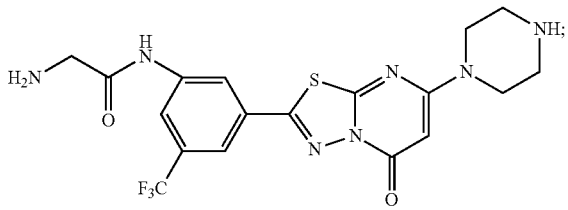

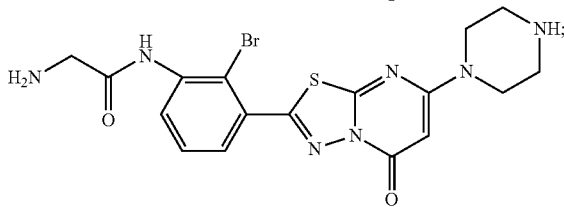

55
-continued
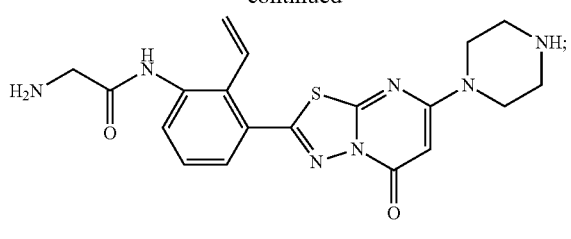
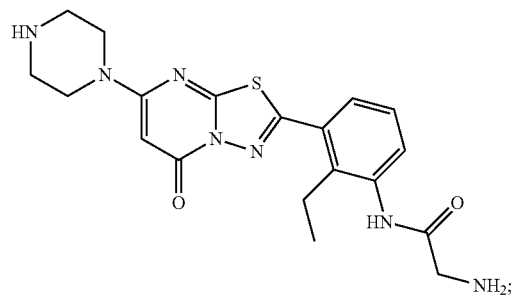
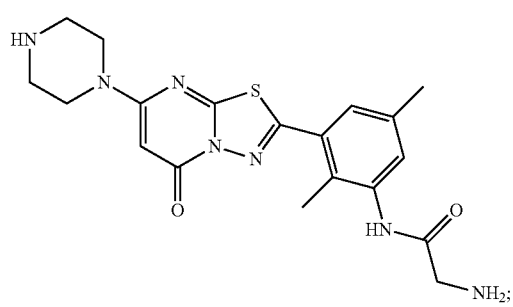
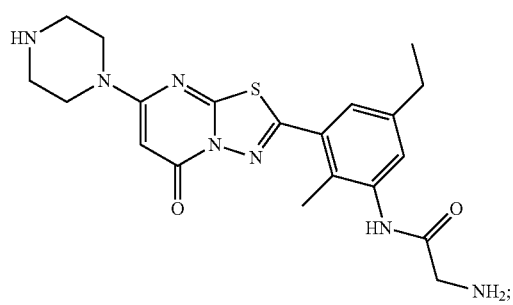
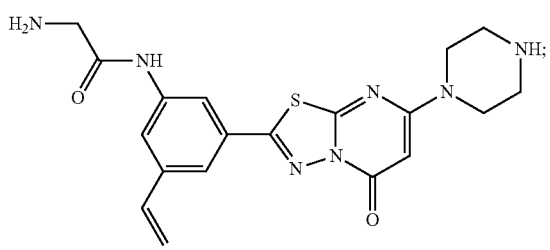
56
-continued
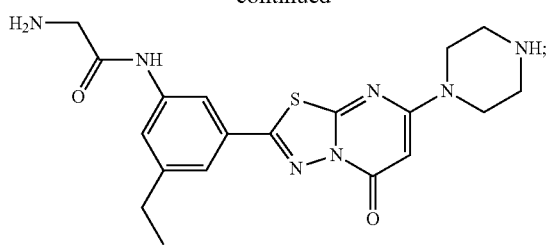
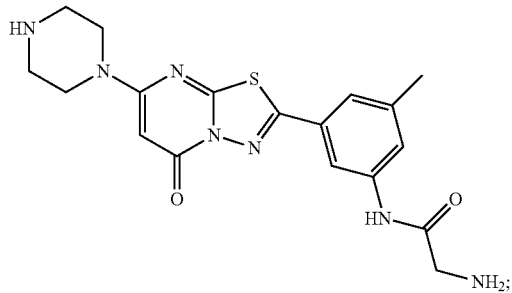
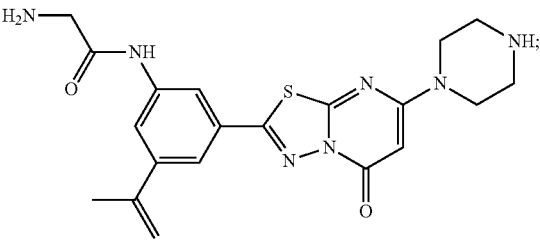
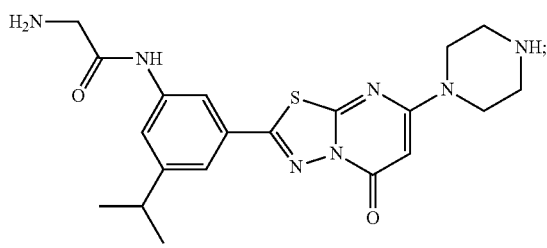

-continued and

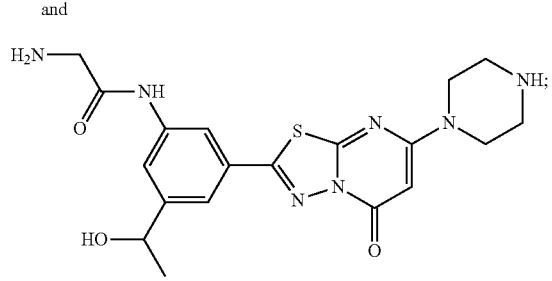

in free or salt form.

5. A compound of Formula P-II, in free or salt form:

Formula P-II

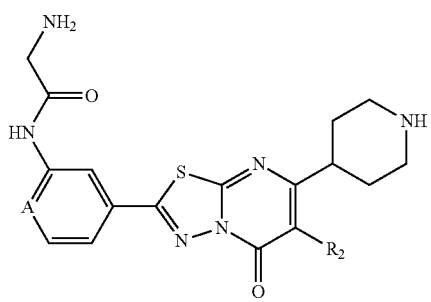

wherein:
A is carbon or nitrogen; and
R₂ is H or halo.

6. The compound according to claim 5, which is selected from:

Formula II

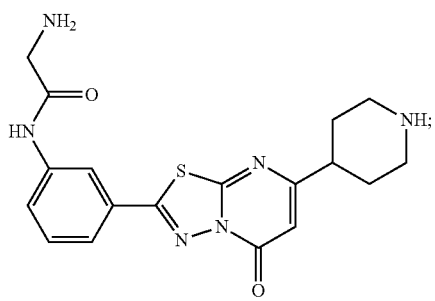

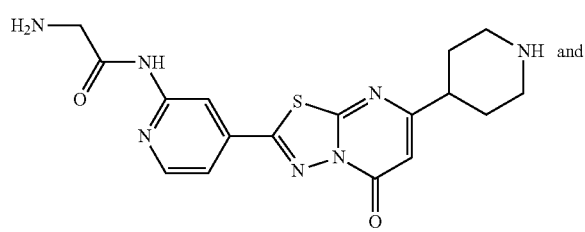

-continued

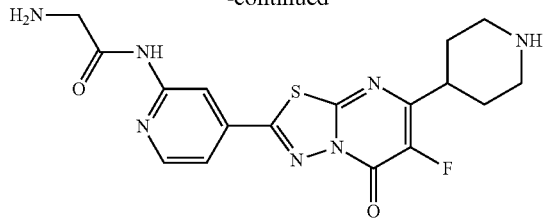

in free or salt form.

7. A compound of salt thereof of claim 1, wherein the compound is

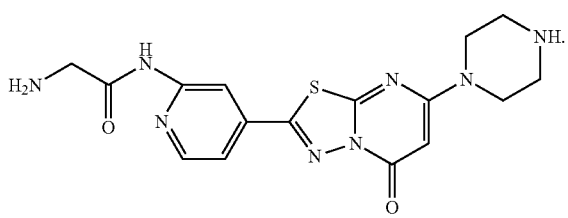 [SMILES: NCC(=O)Nc1cc(-c2nn3c(=O)cc(N4CCNCC4)nc3s2)ccn1]

8. A compound of salt thereof of claim 1, wherein the compound is

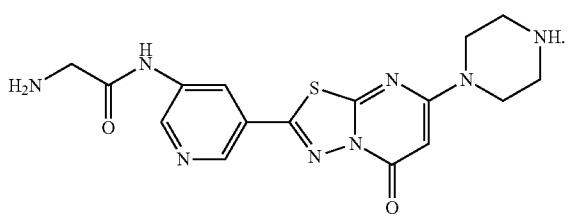 [SMILES: NCC(=O)Nc1cncc(-c2nn3c(=O)cc(N4CCNCC4)nc3s2)c1]

9. A compound of salt thereof of claim 1, wherein the compound is

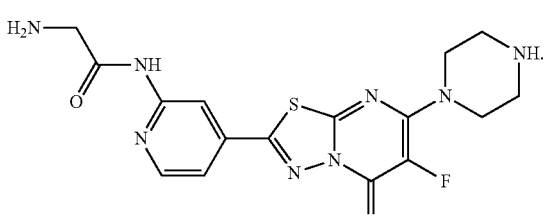

10. A pharmaceutical composition comprising the compound of claim 1, in combination or association with a pharmaceutically acceptable diluent or carrier.

11. A method for the treatment of a thrombotic disorder comprising administering to a subject at risk of thrombotic disorder an effective amount of the compound of claim 1, in free or pharmaceutically acceptable salt form, such that platelet aggregation and/or adhesion is reduced.

12. The method according to claim 11, wherein both platelet aggregation and adhesion are reduced.

13. The method of claim 11, wherein said thrombotic disorders is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

14. The method of claim 11, wherein said thrombotic disorder is thrombosis induced by peripheral vascular surgery.

15. The method of claim 11, further comprises administering to said subject an effective amount of at least one therapeutic agent selected from a group consisting of anti-coagulant, antiplatelet, and fibrinolytic agents in conjunction with the compound according to claim 1, in free or pharmaceutically acceptable salt form.

16. The method according to claim 12, wherein said therapeutic agent is selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, ticagrelor, abciximab, eptifibatide and tirofiban.

17. The method of claim 11, further comprising administering heparin.

18. A method for inhibiting or reducing platelet aggregation and adhesion comprising administering an effective amount of the compound of claim 1, in free or pharmaceutically acceptable salt form, such that platelet aggregation and adhesion is reduced.

19. A method for the treatment of a thrombotic disorder comprising administering to a subject having a thrombotic disorder or at risk of a thrombotic disorder an effective amount of the compound of claim 2, in free or pharmaceutically acceptable salt form, such that platelet aggregation and/or adhesion is reduced.

20. A method for the treatment of a thrombotic disorder comprising administering to a subject having a thrombotic disorder or at risk of a thrombotic disorder an effective amount of the compound of claim 5, in free or pharmaceutically acceptable salt form, such that platelet aggregation and/or adhesion is reduced.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Homo Sapiens

<400> SEQUENCE: 1

His His Leu Gly Gly Ala Lys Gln Ala Gly Asp Val
1               5                   10
```